United States Patent
Li et al.

(10) Patent No.: US 12,201,713 B2
(45) Date of Patent: Jan. 21, 2025

(54) PERSONAL CARE COMPOSITIONS

(71) Applicant: Colgate-Palmolive Company, New York, NY (US)

(72) Inventors: Min Li, Bridgewater, NJ (US); Aixing Fan, Bridgewater, NJ (US); Nadia Soliman, East Brunswick, NJ (US); Komal Shahani, Edison, NJ (US); Junhong Mao, Plainsboro, NJ (US); Thomas Boyd, Metuchen, NJ (US); Amira Khan, East Windsor, NJ (US); Mavis Dennis, Sayreville, NJ (US); Stephy Qianwen Chung, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 17/901,710

(22) Filed: Sep. 1, 2022

(65) Prior Publication Data

US 2023/0225955 A1    Jul. 20, 2023

Related U.S. Application Data

(60) Provisional application No. 63/239,624, filed on Sep. 1, 2021.

(51) Int. Cl.
| | | |
|---|---|---|
| A61K 8/73 | (2006.01) | |
| A61K 8/34 | (2006.01) | |
| A61K 8/365 | (2006.01) | |
| A61Q 19/00 | (2006.01) | |

(52) U.S. Cl.
CPC ............ *A61K 8/73* (2013.01); *A61K 8/342* (2013.01); *A61K 8/365* (2013.01); *A61Q 19/007* (2013.01); *A61K 2800/85* (2013.01)

(58) Field of Classification Search
None
See application file for complete search history.

(56) References Cited

U.S. PATENT DOCUMENTS

| | | | |
|---|---|---|---|
| 2,350,047 A | 5/1944 | Emil et al. | |
| 5,262,153 A | 11/1993 | Mishima et al. | |
| 5,618,522 A | 4/1997 | Deckner et al. | |
| 5,785,962 A | 7/1998 | Hinz et al. | |
| 6,017,548 A | 1/2000 | Epstein et al. | |
| 6,139,850 A | 10/2000 | Hahn et al. | |
| 6,365,137 B1 | 4/2002 | Aust et al. | |
| 7,250,174 B2 | 7/2007 | Lee et al. | |
| 8,227,426 B2 | 7/2012 | Gupta et al. | |
| 8,435,955 B2 | 5/2013 | Masui et al. | |
| 8,673,327 B2 | 3/2014 | Lemoine et al. | |
| 8,741,357 B2 | 6/2014 | Lamy et al. | |
| 8,802,065 B2 | 8/2014 | Oshimura et al. | |
| 8,933,131 B2 | 1/2015 | Carter et al. | |
| 8,992,898 B2 | 3/2015 | Klingman | |
| 9,566,223 B2 | 2/2017 | Klingman | |
| 9,668,948 B2 | 6/2017 | Klingman | |
| 9,713,604 B2 | 7/2017 | Dreher | |
| 10,071,103 B2 | 9/2018 | Sengupta et al. | |
| 10,406,085 B2 | 9/2019 | Dubovoy et al. | |
| 10,532,014 B2 | 1/2020 | Lesniak et al. | |
| 10,638,755 B2 | 5/2020 | Pesaro et al. | |
| 10,864,147 B2 | 12/2020 | Hilliard, Jr. et al. | |
| 10,933,000 B2 | 3/2021 | Hilliard, Jr. et al. | |
| 11,104,868 B2 | 8/2021 | Hardy et al. | |
| 11,331,253 B2 | 5/2022 | Fan | |
| 2003/0053970 A1 | 3/2003 | Bruening et al. | |
| 2004/0076654 A1 | 4/2004 | Gamble | |
| 2006/0182708 A1 | 8/2006 | Bockmuhl et al. | |
| 2007/0167529 A1 | 7/2007 | Walton et al. | |
| 2007/0243155 A1 | 10/2007 | Bottiglieri et al. | |
| 2008/0187562 A1 | 8/2008 | Fan et al. | |
| 2008/0206170 A1 | 8/2008 | Nivaggioli et al. | |
| 2008/0299068 A1 | 12/2008 | Omura et al. | |
| 2010/0189753 A1 | 7/2010 | Van Bavel et al. | |
| 2012/0006348 A1 | 1/2012 | Grollier et al. | |
| 2013/0059929 A1 | 3/2013 | Koehler et al. | |
| 2014/0205555 A1 | 7/2014 | Gale et al. | |
| 2015/0050227 A1 | 2/2015 | Liu et al. | |
| 2015/0202136 A1 | 7/2015 | Lanzalaco et al. | |
| 2016/0151257 A1 | 6/2016 | Klingman | |
| 2017/0181950 A1* | 6/2017 | Wu | A61K 8/365 |
| 2017/0183452 A1 | 6/2017 | Panandiker et al. | |
| 2018/0177692 A1 | 6/2018 | Garcia et al. | |

(Continued)

FOREIGN PATENT DOCUMENTS

| | | |
|---|---|---|
| CN | 101107045 | 1/2008 |
| CN | 101182299 | 5/2008 |

(Continued)

OTHER PUBLICATIONS

Evans et al., 2012, "Axillary skin biology and care", International Journal of Cosmetic Science, 34:389-395.
IFSCC, 1998, Antiperspirants-and-Deodorants: Principles of Underarm Technology, Micelle press IFSCC No. 6, pp. 1-61.
International Search Report and the Written Opinion of the International Searching Authority issued in International Application PCT/US2022/042563 mailed Jan. 20, 2023.
Johnson, 2022, "How to Best Treat Acne Scars," Medical News Today (online website: [(https://www.medicalnewstoday.com/articles/324784, pp. 1-14)].
Laboratoire SVR, 2017, "48H Anti-Perspirant Deodorant Roll-on", Mintel Database GNPD AN: 5111953.

(Continued)

*Primary Examiner* — Nicole P Babson

(57) ABSTRACT

Described herein are personal care compositions that may include from about 0.1 to about 5 wt. % of a polysaccharide; from about 0.01 to about 12 wt. % of a fatty alcohol; and from about 0.5 to about 7 wt. % of a post-biotic blend, wherein all weight percentages are based on the total weight of the personal care composition. Methods of making and using these personal care compositions are also described herein.

17 Claims, 21 Drawing Sheets

(56) References Cited

U.S. PATENT DOCUMENTS

| | | | |
|---|---|---|---|
| 2019/0183780 A1 | 6/2019 | Pan et al. | |
| 2019/0270951 A1 | 9/2019 | Hardy et al. | |
| 2020/0016053 A1 | 1/2020 | Hilliard, Jr. et al. | |
| 2020/0129405 A1* | 4/2020 | Mitchell | A61K 8/36 |
| 2020/0405674 A1 | 12/2020 | Schiller et al. | |
| 2021/0275418 A1 | 9/2021 | Bhardwaj | |
| 2021/0275419 A1 | 9/2021 | Li et al. | |
| 2021/0283025 A1 | 9/2021 | Das et al. | |
| 2021/0299020 A1 | 9/2021 | Cruz et al. | |
| 2022/0031591 A1 | 2/2022 | Botto et al. | |
| 2022/0079854 A1 | 3/2022 | Li | |
| 2022/0241162 A1 | 8/2022 | Fan et al. | |
| 2022/0395437 A1 | 12/2022 | Leva | |

FOREIGN PATENT DOCUMENTS

| | | |
|---|---|---|
| CN | 101820753 | 9/2010 |
| CN | 103690380 | 4/2014 |
| CN | 109259188 | 1/2019 |
| DE | 19643585 | 4/1998 |
| DE | 102004032734 | 10/2005 |
| EP | 0345082 | 12/1989 |
| EP | 0749749 | 12/1996 |
| EP | 1443892 | 8/2004 |
| EP | 1510200 | 3/2005 |
| EP | 1526827 | 5/2005 |
| EP | 2353579 | 8/2011 |
| EP | 2374835 | 10/2011 |
| JP | H09110650 | 4/1997 |
| JP | 2004-089177 | 3/2004 |
| KR | 20120070104 | 6/2012 |
| KR | 101189187 | 10/2012 |
| KR | 20140039548 | 4/2014 |
| KR | 20150011060 | 1/2015 |
| KR | 101503979 | 3/2015 |
| KR | 101768921 | 8/2017 |
| WO | 2009/020582 | 2/2009 |
| WO | 2009/046008 | 4/2009 |
| WO | 2010/044076 | 4/2010 |
| WO | 2011/099849 | 8/2011 |
| WO | 2017/030560 | 2/2017 |
| WO | 2018/022016 | 2/2018 |
| WO | 2019/117858 | 6/2019 |
| WO | 2020/052916 | 3/2020 |
| WO | 2020/057761 | 3/2020 |
| WO | 2020/185654 | 9/2020 |
| WO | 2021/096518 | 5/2021 |
| WO | 2021/183462 | 9/2021 |
| WO | 2021/183464 | 9/2021 |
| WO | 2022/063857 | 3/2022 |

OTHER PUBLICATIONS

Anonymous, "Ingredients of Filorga Ultimate Revitalizing Night Cream," retrieved from https://www.cosdna.com/chs/cosmetic_4251189624.html, published on May 16, 2015.

Anonymous, 2021, "Atopicare Shower Cream", Mintel Database GNPD AN: 8747223.

International Search Report and the Written Opinion of the International Searching Authority issued in International Application PCT/US2022/042327 mailed Dec. 20, 2022.

Allies Group, 2017, "Promise Keeper Blemish Facial", Mintel Database GNPD AN: 5196555.

Anonymous, 2005, "Intensity Classic Deo Roll-On", Mintel Database GNPD AN: 371579.

Anonymous, 2006, "Micro Exfoliating Oxygenating Gel", Mintel Database GNPD AN: 598917.

Anonymous, 2011, "E.V.E. Essential Vital Elements Serum Source", Mintel Database GNPD AN: 1666406.

Anonymous, 2011, "Milk Body Lotion", Mintel Database GNPD AN: 1632704.

Anonymous, 2012, "Super-Mud Clearing Treatment", Mintel Database GNPD AN: 1921209.

Anonymous, 2014, "Clinical Concentrate Radiance Booster", Mintel Database GNPD AN: 2350479.

Anonymous, 2014, "Intimate Wash", Mintel Database GNPD AN: 2677521.

Anonymous, 2017, "Acne on The Spot Serum", Mintel Database GNPD AN: 4688909.

Anonymous, 2018, "Shaveless Hair Minimizing Anti-Perspirant Deodorant Roll-On", Mintel Database GNPD AN: 5574907.

Anonymous, 2019, "Superserum 6-Acid Refining Treatment", Mintel Database GNPD AN: 6521601.

Anonymous, 2019, "Supertoner Exfoliating Acid Soution", Mintel Database GNPD AN: 6457009.

Boyd (https://www.chemservice.com/news/2014/08/which-chemicals-make-deodorants-and-antiperspirants-work/), Aug. 22, 2014, pp. 1-2 (Year:2014).

International Search Report and the Written Opinion of the International Searching Authority issued in International Application PCT/US2019/061522 mailed May 12, 2020.

International Search Report and the Written Opinion of the International Searching Authority issued in International Application PCT/US2020/021657 mailed May 27, 2020.

International Search Report and the Written Opinion of the International Searching Authority issued in International Application PCT/US2021/021426 mailed Jun. 28, 2021.

International Search Report and the Written Opinion of the International Searching Authority issued in International Application PCT/US2021/021428 mailed Jun. 28, 2021.

Cosinter, 2011, "Intimate Liquid Soap", Mintel Database GNPD AN: 1547745.

Do Couto et al., 2016, "Antifungal Activity of the Piroctone Olamine in Intra-Abdominal Candidiasis", Spinger Plus, 5:468.

IFSCC Monograph, No. 6, "Antiperspirants-and-Deodorants: Principles of Underarm Technology," Micelle Press, 76 pages, 1998.

International Search Report and the Written Opinion of the International Searching Authority issued in International Application PCT/US2023/031519 mailed Nov. 30, 2023.

International Search Report and the Written Opinion of the International Searching Authority issued in International Application PCT/US2023/031632 mailed Nov. 30, 2023.

Pharma Solutions, 2022, "Cleansing Bar", Mintel Database GNPD AN: 9713532.

Cork, 1996, "The role of *Staphylococcus aureus* in atopic eczema: treatment strategies", Journal of the European Academy of Dermatology and Venereology, vol. 7, Suppl. 1, pp. 31-37.

Patel, 2014, "Postinflammatory hyperpigmentation: Review of pathogenesis, prevention, and treatment", Pigment International, vol. 1, Issue 2, pp. 59-69.

Celltrion Skincure, 2021, "Cleansing Oil & Blackhead", Mintel Database GNPD AN: 8549187.

Coreana Cosmetics, 2020, "Peeling Pad", Mintel Database GNPD AN: 7440987.

International Search Report and the Written Opinion of the International Searching Authority issued in International Application PCT/US2023/084725 mailed Mar. 28, 2024.

* cited by examiner

Comp. Ex. 1　　　　　　　　Ex. A　　　　　　　　Comp. Ex. 3

PERSONAL CARE COMPOSITIONS

CROSS-REFERENCE TO RELATED APPLICATION

This application claims the benefit of priority from U.S. Provisional Application No. 63/239,624, entitled "Personal Care Compositions" and filed Sep. 1, 2021, the contents of which are hereby incorporated herein in its entirety.

BACKGROUND

Skin is the body's first line of defense against infections and environmental stressors. It acts as a major physical and immunological protective barrier, but also plays a critical role in temperature regulation, water holding, vitamin D production, and sensing. Its outermost surface consists of a lipid- and protein-laden cornified layer dotted with hair follicles and eccrine glands that secrete lipids, antimicrobial peptides (AMPs), enzymes, salts, etc. It harbors microbial communities living in a range of physiologically and anatomically distinct niches. Overall, this constitutes a highly heterogeneous and complex system.

During adulthood, absent any specific skin condition, the skin microbiome remains relatively stable, despite the large inter-individual variability, suggesting that mutualistic and commensal interactions exist among microbes and between microbes and host, even for bacterial species often considered as opportunistic pathogens. Under healthy skin conditions, most of the microbes living on the skin behave as commensal or mutualistic organisms. Through various mechanisms, such as the stimulation of innate factor secretion or antimicrobial peptides (AMPs), they maintain the microflora composition avoiding the spread of opportunistic parasites, while also contributing to the education of the immune system and to healthy skin barrier homeostasis. In case of barrier breach or immunosuppression, these carefully balanced relationships may transition from commensalism to pathogenicity, a transition referred to as dysbiosis, enabling the overgrowth of pathogenic species, common in skin conditions such as acne, psoriasis, ulcer, and atopic dermatitis.

Probiotics are known to have beneficial effects on skin microflora balance. In particular, it is desirable to inhibit harmful bacteria, while promoting the growth of beneficial bacteria. However, the ability to provide this dual benefit still remains a challenge.

In addition, skin tends to lose its elasticity and/or firmness as it ages. Current options for maintaining skin elasticity and firmness are sub-optimal.

As such, embodiments of the present invention are designed to provide these, and other, benefits.

BRIEF SUMMARY

The present disclosure relates to personal care compositions containing post-biotic blends for rebalancing skin microbiome. The inventors discovered that personal care compositions formulated to have specific components in certain ratios provide synergistic benefits to the skin microbiome, including, e.g., reducing undesirable bacteria and increasing desirable bacteria. For instance, the personal care compositions disclosed herein may reduce undesirable bacteria on the skin, such as *E. coli* and odor causing bacteria (e.g., *Corynebacterium striatum*), while simultaneously promoting the growth of desirable bacteria, such as *Staphylococcus epidermidis*.

The personal care compositions may be formulated as leave-on compositions or as rinse-off compositions. In some cases, the personal care compositions may contain a prebiotic component and a post-biotic blend component.

Aspects of the disclosure also relate to methods for improving skin using such personal care compositions. In at least some embodiments, the method includes using two or more personal care compositions. For instance, the method may include applying a cleaning composition to a section of skin, rinsing the section of skin, and applying a lotion composition to the section of skin. Additionally or alternatively, the personal care compositions according to embodiments of the disclosure may improve skin barrier function and hydration.

In accordance with an aspect of the invention, provided is a personal care composition including: from about 0.1 to about 5 wt. % of a polysaccharide; from about 0.01 to about 12 wt. % of a fatty alcohol; and from about 0.5 to about 7 wt. % of a post-biotic blend, wherein all weight percentages are based on the total weight of the personal care composition.

According to another aspect of the invention, provided is a personal care composition including: from about 0.1 to about 5 wt. % of a polysaccharide comprises carrageenan, inulin, or a mixture thereof; from about 2 to about 12 wt. % of a fatty alcohol; from about 0.5 to about 10 wt. % of a fatty ester; and from about 0.5 to about 7 wt. % of a post-biotic blend selected from lactic acid, pyruvic acid, acetic acid, butanedioic acid, succinic acid, formic acid, propionic acid, butyric acid, isobutyric acid, valeric acid, isovaleric acid, lactic acid, pyruvic acid, a derivative thereof, a salt thereof, and a combination of two or more thereof, wherein all weight percentages are based on the total weight of the personal care composition.

In accordance with a further aspect of the invention, provided is a method for improving skin. In some embodiments, the method includes applying a cleaning composition to a section of skin, the cleaning composition comprising: from about 1 to about 25 wt. % of a surfactant, from about 0.1 to about 5 wt. % of a polysaccharide, from about 0.01 to about 5 wt. % of a fatty alcohol, and from about 0.5 to about 7 wt. % of a post-biotic blend, wherein all weight percentages are based on the total weight of the cleaning composition; rinsing the section of skin; applying a lotion composition to the section of skin, the lotion comprising: from about 1 to about 30 wt. % of a silicone, an oil, a polyol, an emollient or a combination thereof, from about 0.1 to about 5 wt. % of a polysaccharide, from about 0.01 to about 5 wt. % of a fatty alcohol, and from about 0.5 to about 7 wt. % of a post-biotic blend, wherein all weight percentages are based on the total weight of the lotion composition.

According to yet another aspect of the invention, provided is use of a personal care composition for alleviate suffering and/or damaged skin including: from about 0.1 to about 5 wt. % of a polysaccharide; from about 0.01 to about 12 wt. % of a fatty alcohol; and from about 0.5 to about 7 wt. % of a post-biotic blend, wherein all weight percentages are based on the total weight of the personal care composition.

DETAILED DESCRIPTION

Figure 1A:
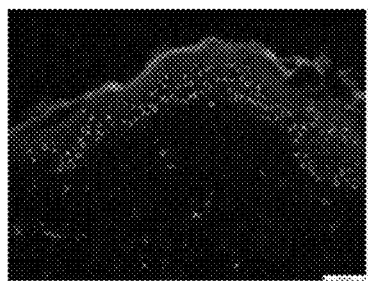
FIG. 1A depicts the penetration of dye into skin samples after receiving an application of an exemplary personal care composition or comparative personal care compositions in accordance with an aspect of the invention.
Figure 1A:
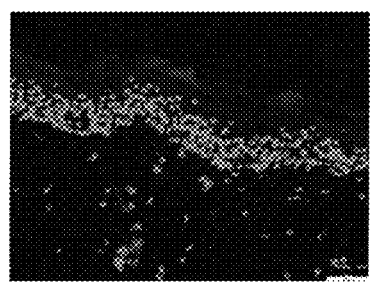
Figure 1A:
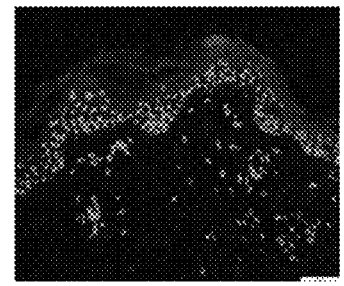

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation.

As used herein, the term "SCFA Blend" is intended to refer to any combination of short chain fatty acids described herein.

As used herein and in the appended claims, the singular forms "a", "an", and "the" include plural references unless the context dictates otherwise. The singular form of any class of the ingredients refers not only to one chemical species within that class, but also to a mixture of those chemical species. The terms "a" (or "an"), "one or more" and "at least one" may be used interchangeably herein. The terms "comprising", "including", and "having" may be used interchangeably. The term "include" should be interpreted as "include, but are not limited to". The term "including" should be interpreted as "including, but are not limited to".

As used throughout, ranges are used as shorthand for describing each and every value that is within the range. Any value within the range can be selected as the terminus of the range. Thus, a range from 1-5, includes specifically 1, 2, 3, 4 and 5, as well as sub ranges such as 2-5, 3-5, 2-3, 2-4, 1-4, etc.

The term "about" when referring to a number means any number within a range of 10% of the number. For example, the phrase "about 2.0 wt. %" refers to a number between and including 1.800 wt. % and 2.200 wt. %.

All references cited herein are hereby incorporated by reference in their entireties. In the event of a conflict in a definition in the present disclosure and that of a cited reference, the present disclosure controls.

The weight percentages expressed herein are based on the amount of active in a particular composition or formula, not necessarily the amount of an ingredient added to the formula, as certain ingredients contain inactive components (e.g., water).

The abbreviations and symbols as used herein, unless indicated otherwise, take their ordinary meaning. The abbreviation "wt. %" means percent by weight with respect to the personal care composition. The symbol "0" refers to a degree, such as a temperature degree or a degree of an angle. The symbols "h", "min", "mL", "nm", "µm" mean hour, minute, milliliter, nanometer, and micrometer, respectively. The abbreviation "UV-VIS" as referring to a spectrometer or spectroscopy, means Ultraviolet-Visible. The abbreviation "rpm" means revolutions per minute.

The phrase "MRS agar" refers to De Man, Rogosa and Sharpe agar, which is a selective culture medium designed to favor the growth of *Lactobacillus*. The phrase "TSB medium" refers to tryptic soy broth or trypticase soy broth, which is used in microbiology laboratories as a culture broth to grow aerobic bacteria. The phrase "PBS wash" refers to phosphate-buffered saline wash. The abbreviation "qPCR" is quantitative polymerase chain reaction.

When referring to chemical structures, and names, the symbols "C", "H", and "O" mean carbon, hydrogen, and oxygen, respectively. The symbols "—", "=" and "≡" mean single bond, double bond, and triple bond, respectively.

Any member in a list of species that are used to exemplify or define a genus, may be mutually different from, or overlapping with, or a subset of, or equivalent to, or nearly the same as, or identical to, any other member of the list of species. Further, unless explicitly stated, such as when reciting a Markush group, the list of species that define or exemplify the genus is open, and it is given that other species may exist that define or exemplify the genus just as well as, or better than, any other species listed.

All components and elements positively set forth in this disclosure can be negatively excluded from the claims. In other words, the hair cleansing compositions of the instant disclosure can be free or essentially free of all components and elements positively recited throughout the instant disclosure. In some instances, the hair cleansing compositions of the present disclosure may be substantially free of non-incidental amounts of the ingredient(s) or compound(s) described herein. A non-incidental amount of an ingredient or compound is the amount of that ingredient or compound that is added into the personal care composition by itself. For example, a personal care composition may be substantially free of a non-incidental amount of an ingredient or compound, although such ingredient(s) or compound(s) may be present as part of a raw material that is included as a blend of two or more compounds.

Some of the various categories of components identified may overlap. In such cases where overlap may exist and the hair cleansing composition includes both components (or the composition includes more than two components that overlap), an overlapping compound does not represent more than one component. For example, certain compounds may be characterized as both an emulsifier and a surfactant. If a particular hair composition includes both an emulsifier and a surfactant, the compounds that may be characterized as both an emulsifier and a surfactant will serve only as either the emulsifier or the surfactant—not both.

For readability purposes, the chemical functional groups are in their adjective form; for each of the adjectives, the word "group" is assumed. For example, the adjective "alkyl" without a noun thereafter, should be read as "an alkyl group".

*Escherichia coli* is a Gram-negative, facultative anaerobic, rod-shaped, coliform bacterium of the genus *Escherichia* that is commonly found in the lower intestine of warm-blooded organisms (endotherms). Most *E. coli* strains are harmless, but some serotypes can cause serious food poisoning in their hosts, and are occasionally responsible for product recalls due to food contamination.

*Staphylococcus aureus* is a Gram-positive, round-shaped bacterium that is a member of the Firmicutes, and it is a usual member of the microbiota of the body, frequently found in the upper respiratory tract and on the skin. It is often positive for catalase and nitrate reduction and is a facultative anaerobe that can grow without the need for oxygen. Skin infections are the most common form of *S. aureus* infection. This can manifest in various ways, including small benign boils, folliculitis, impetigo, cellulitis, and more severe, invasive soft-tissue infections.

*S. aureus* is extremely prevalent in persons with atopic dermatitis, more commonly known as eczema. It is mostly found in fertile, active places, including the armpits, hair, and scalp. Large pimples that appear in those areas may exacerbate the infection if lacerated. This can lead to staphylococcal scalded skin syndrome, a severe form of which can be seen in newborns.

*Staphylococcus epidermidis*, a Gram-positive bacterium, is a part of the normal human flora, typically the skin flora, and less commonly the mucosal flora. It is a facultative anaerobic bacteria.

Further tests of adding 0.6 wt. % SCFA Blend into a commercially available body wash and application thereof to a skin tissue, showed the body wash to upregulate hydration related gene and tight junction gene and down-regulated inflammation related gene expressions. This revolutionary technology is suitable for body wash, lotion, or underarm products and for providing skin microbiome benefits.

Aspects of the present invention relate to personal care compositions containing post-biotic blends for rebalancing skin microbiome. The inventors discovered that personal care compositions formulated to have specific components in certain ratios provide synergistic benefits to the skin microbiome, including, e.g., reducing undesirable bacteria and increasing desirable bacteria. For instance, the personal care compositions disclosed herein may reduce undesirable bacteria on the skin, such as *E. coli* and odor producing bacteria (e.g., *Corynebacterium striatum*), while simultaneously promoting the growth of desirable bacteria, such as *Staphylococcus epidermidis*. It was also discovered that certain personal care compositions exhibited surprising anti-dandruff properties, including a reduction in growth of *M. restricta* while providing an increase in the growth of *S. epidermidis*.

The personal care compositions may be formulated as leave-on compositions or as rinse off compositions. In some cases, the personal care compositions may contain a prebiotic component and a post-biotic blend component.

Aspects of the disclosure also relate to methods for improving skin using such personal care compositions. In at least some embodiments, the method includes using two or more personal care compositions. For instance, the method may include applying a cleaning composition to a section of skin, rinsing the section of skin, and applying a lotion composition to the section of skin. In at least one embodiment, the method comprises administering to the skin a personal care composition in an amount effective to promote the growth of beneficial bacteria and inhibit the growth of harmful bacteria, wherein the beneficial bacterium is selected from the group consisting of *S. epidermidis*, and harmful bacteria is selected from the group consisting of *E. coli*, *C. striatum*, and *S. aureus*. Additionally, or alternatively, the personal care compositions according to embodiments of the disclosure may improve skin barrier function and hydration.

In certain embodiments, the personal care composition has a viscosity of from about 50,000 to 120,000 centipoise (cP), about 60,000 to 110,000 centipoise (cP), about 70,000 to 90,000 centipoise (cP), including all values in between these ranges, at room temperature using Brookfield viscometer and a spindle no. 3. In some embodiments, the personal care composition is a body wash having a viscosity of from about 2,000 to about 20,000 cP, as measured using Brookfield viscometer spindle no. 4 at rpm 20. In other embodiments, the personal care composition is a body lotion having a viscosity of greater than about 15,000 cP, as measured using Brookfield viscometer spindle no. 93 at rpm 10. In certain embodiments, the personal care composition has a viscosity of from about 2,000 to about 20,000 cP, or about 3,000 to about 16,000 cP, or about 4,000 to about 12,000 cP, including all values in between these ranges, including all values in between these ranges, at room temperature using Brookfield viscometer and a spindle no. 3.

The personal care composition may, preferably, be formulated to inhibit and/or reduce the growth of *C. striatum, E. coli, S. aureus*, and *M. restricta* while increasing the growth of *S. epidermidis*. For example, the personal care compositions may inhibit the growth of *C. striatum, E. coli, S. aureus*, and/or *M. restricta* by about 5% or more (cumulatively or individually) and increase the growth of *S. epidermidis* by about 5% or more by counting CFU/mL after incubating a 2 ml of a bacterial culture having a 0.1 optical density at 610 nm using a UV-VIS Spectrometer for *C. striatum, S. aureus, E. coli, M. restricta* and *S. epidermidis* with a 2 ml of 1% personal care product at a temperature of 37° C. for 3 hours. In some embodiment, the personal are care composition may inhibit the growth of *C. striatum, E. coli, S. aureus*, and/or *M. restricta*, cumulatively or individually, by about 5% or more, about 7% or more, about 10% or more, about 13% or more, about 16% or more, about 19% or more, about 23% or more, about 27% or more, or any range thereof. Additionally or alternatively, certain embodiments of the personal care composition may increase the growth of *S. epidermidis* by about 5% or more, about 7% or more, about 10% or more, about 13% or more, about 16% or more, about 19% or more, about 23% or more, about 27% or more, or any range thereof.

In at least one embodiment, the personal care composition is formulated to inhibit the growth of *C. striatum* and *E. coli* (cumulatively or individually) by about 5% or more and increase the growth of *S. epidermidis* by about 5% or more by counting CFU/mL after incubating a 2 ml of a bacterial culture having a 0.1 optical density at 610 nm using a UV-VIS Spectrometer for *C. striatum, E. coli*, and *S. epidermidis* with a 2 ml of 1% personal care product at a temperature of 37° C. for 3 hours.

In at least one embodiment, the personal care composition is formulated to inhibit the growth of *M. restricta* by about 5% or more and increase the growth of *S. epidermidis* by about 5% or more by counting CFU/mL after incubating a 2 ml of a bacterial culture having a 0.8 ml and 0.38 optical density at 610 nm using a UV-VIS Spectrometer for *M. restricta* and *S. epidermidis*, respectively, with a 2 ml of 1% personal care product at a temperature of 37° C. for 3 hours.

In at least one embodiment, the personal care composition is formulated to inhibit the growth of *S. aureus* by about 5% or more and increase the growth of *S. epidermidis* by about 5% or more by counting CFU/mL after incubating a 2 ml of a bacterial culture having a 0.1 optical density at 610 nm using a UV-VIS Spectrometer for *S. aureus* and *S. epidermidis* with a 2 ml of 1% personal care product at a temperature of 37° C. for 3 hours.

Preferably, the personal care compositions may be formulated to inhibit the growth of *C. striatum* and *E. coli* and increase the growth of *S. epidermidis*, such that the ratio of *S. epidermidis* to *C. striatum* and *E. coli* is about 1.5 or more, based on a log count of *C. striatum* and *E. coli* divided by a log count of *S. epidermidis* after incubating a 2 ml of a bacterial culture having a 0.1 optical density at 610 nm using a UV-VIS Spectrometer for *C. striatum* and *E. coli* and *S. epidermidis* with a 2 ml of 1% personal care product at a temperature of 37° C. for 3 hours. For example, the personal care composition may inhibit the growth of *C. striatum* and *E. coli* and increase the growth of *S. epidermidis*, such that the ratio of *S. epidermidis* to *C. striatum* and *E. coli* is about 1.5 or more, about 1.75 or more, about 2 or more, about 2.3 or more, about 2.6 or more, about 2.9 or more, about 3.1 or more, about 3.4 or more, or any range thereof.

In some embodiments, the personal care composition is formulated to inhibit the growth of *C. striatum* and increase the growth of *S. epidermidis*, such that the ratio of *S. epidermidis* to *C. striatum* is about 2 or more, based on a log count of *C. striatum* divided by a log count of *S. epidermidis* after incubating a 2 ml of a bacterial culture having a 0.1 optical density at 610 nm using a UV-VIS Spectrometer for *C. striatum* and *S. epidermidis* with a 2 ml of 1% personal care product at a temperature of 37° C. for 3 hours.

In yet further embodiments, the personal care composition is formulated to inhibit the growth of *C. striatum* and *E. coli* and increase the growth of *S. epidermidis*, such that the ratio of *S. epidermidis* to a total of *C. striatum* and *E. coli* is about 2 or more, based on a log count of *C. striatum* and *E. coli* divided by a log count of *S. epidermidis* after incubating a 2 ml of a bacterial culture having a 0.1 optical density at 610 nm using a UV-VIS Spectrometer for *C. striatum, E. coli*, and *S. epidermidis* with a 2 ml of 1% personal care product at a temperature of 37° C. for 3 hours.

The personal care compositions may be formulated to inhibit the growth of *M. restricta* and increase the growth of *S. epidermidis*, such that the ratio of *S. epidermidis* to *M. restricta* is about 1.5 or more, based on a log count of *M. restricta* divided by a log count of *S. epidermidis* after incubating a 2 ml of a bacterial culture having a 0.8 and 0.38 optical density at 610 nm using a UV-VIS Spectrometer for *M. restricta* and *S. epidermidis*, respectively with a 2 ml of 1% personal care product at a temperature of 37° C. for 3 hours. For example, the personal care composition may inhibit the growth of *M. restricta* and increase the growth of *S. epidermidis*, such that the ratio of *S. epidermidis* to *M. restricta* is about 1.5 or more, about 1.75 or more, about 2 or more, about 2.3 or more, about 2.6 or more, about 2.9 or more, about 3.1 or more, about 3.4 or more, or any range thereof.

In some embodiments, the personal care composition is formulated to inhibit the growth of *M. restricta* and increase the growth of *S. epidermidis*, such that the ratio of *S. epidermidis* to *M. restricta* is about 2 or more, based on a log count of *M. restricta* divided by a log count of *S. epidermidis* after incubating a 2 ml of a bacterial culture having a 0.8 and 0.38 optical density at 610 nm using a UV-VIS Spectrometer for *M. restricta* and *S. epidermidis*, respectively with a 2 ml of 1% personal care product at a temperature of 37° C. for 3 hours.

The personal care compositions may be formulated to inhibit the growth of *S. aureus* and increase the growth of *S. epidermidis*, such that the ratio of *S. epidermidis* to *S. aureus* is about 1.5 or more, based on a log count of *S. aureus* divided by a log count of *S. epidermidis* after incubating a 2 ml of a bacterial culture having a 0.1 optical density at 610 nm using a UV-VIS Spectrometer for *S. aureus* and *S. epidermidis* with a 2 ml of 1% personal care product at a temperature of 37° C. for 3 hours. For example, the personal care composition may inhibit the growth of *S. aureus* and increase the growth of *S. epidermidis*, such that the ratio of *S. epidermidis* to *S. aureus* is about 1.5 or more, about 1.75 or more, about 2 or more, about 2.3 or more, about 2.6 or more, about 2.9 or more, about 3.1 or more, about 3.4 or more, or any range thereof.

In some embodiments, the personal care composition is formulated to inhibit the growth of *S. aureus* and increase the growth of *S. epidermidis*, such that the ratio of *S. epidermidis* to *S. aureus* is about 2 or more, based on a log count of *S. aureus* divided by a log count of *S. epidermidis* after incubating a 2 ml of a bacterial culture having a 0.1 optical density at 610 nm using a UV-VIS Spectrometer for *S. aureus* and *S. epidermidis* with a 2 ml of 1% personal care product at a temperature of 37° C. for 3 hours.

The personal care compositions may be in the form of skin care, hair care, sun care, or nail care compositions. Non-limiting examples of the form of the personal care compositions according to aspects of the invention include a shampoo, a hair conditioner, a lotion, a cream, a serum, a balm, a spray, a deodorant (e.g., a roll-on deodorant, spray deodorant, stick deodorant), an antiperspirant (e.g., a roll-on antiperspirant, spray antiperspirant, stick antiperspirant), a body wash, a shower gel, a bar soap, a soft soap, a sunscreen, a cosmetic, and the like. In some instances, the personal care composition may be in the form of an antidandruff shampoo and/or antidandruff conditioner.

Suitable components, such as those listed below, may be included or excluded from the formulations for the personal care compositions depending on the specific combination of other ingredients, the form of the personal care compositions, and/or the use of the compositions (e.g., a lotion, cream, spray, etc.).

The personal care compositions comprise a polysaccharide(s), typically in an amount of from about 0.1 to about 5 wt. %, based on the total weight of the personal care compositions. The amount of polysaccharide(s) present in the personal care composition may be from about 0.1 to about 5 wt. %, about 0.1 to about 4 wt. %, about 0.1 to about 3.5 wt. %, about 0.1 to about 3 wt. %, about 0.1 to about 2.5 wt. %, about 0.1 to about 2 wt. %, about 0.1 to about 1.5 wt. %, about 0.1 to about 1 wt. %; about 0.25 to about 5 wt. %, about 0.25 to about 4 wt. %, about 0.25 to about 3.5 wt. %, about 0.25 to about 3 wt. %, about 0.25 to about 2.5 wt. %, about 0.25 to about 2 wt. %, about 0.25 to about 1.5 wt. %, about 0.25 to about 1 wt. %; about 0.5 to about 5 wt. %, about 0.5 to about 4 wt. %, about 0.5 to about 3.5 wt. %, about 0.5 to about 3 wt. %, about 0.5 to about 2.5 wt. %, about 0.5 to about 2 wt. %, about 0.5 to about 1.5 wt. %, about 0.5 to about 1 wt. %; about 0.75 to about 5 wt. %, about 0.75 to about 4 wt. %, about 0.75 to about 3.5 wt. %, about 0.75 to about 3 wt. %, about 0.75 to about 2.5 wt. %, about 0.75 to about 2 wt. %, about 0.75 to about 1.5 wt. %; about 1 to about 5 wt. %, about 1 to about 4 wt. %, about 1 to about 3.5 wt. %, about 1 to about 3 wt. %, about 1 to about 2.5 wt. %, about 1 to about 2 wt. %; about 1.25 to about 5 wt. %, about 1.25 to about 4 wt. %, about 1.25 to about 3.5 wt. %, about 1.25 to about 3 wt. %, about 1.25 to about 2.5 wt. %, about 1.25 to about 2 wt. %; about 1.5 to about 5 wt. %, about 1.5 to about 4 wt. %, about 1.5 to about 3.5 wt. %, about 1.5 to about 3 wt. %, about 1.5 to about 2.5 wt. %, about 1.5 to about 2 wt. %, including any ranges and subranges therebetween, based on the total weight of the personal care composition.

Examples of polysaccharide(s) that may be present in the personal care composition include, but are not limited to, cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, carrageenan, tragacanth gum, xanthan gum, biosaccharide gum, inulin, and combinations of two or more thereof.

Preferably, the polysaccharide is fructan, inulin, carrageenan, or a combination of two or more thereof. In one embodiment, the polysaccharide is fructan. In another embodiment, the polysaccharide is inulin. In yet another embodiment, the polysaccharide is carrageenan.

The personal care compositions comprise a fatty alcohol(s), typically in an amount of from about 0.01 to about 12 wt. %, based on the total weight of the personal care compositions. For example, the amount of fatty alcohol(s) present in the personal care composition may be from about 0.01 to about 12 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %; about 0.1 to about 12 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.5 to about 12 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 1 to about 12 wt. %, about 1 to about 10 wt. %, about 1 to about 8 wt. %, about 1 to about 6 wt. %, about 1 to about 5 wt. %, about 1 to about 4 wt. %, about 1 to about 3 wt. %, about 1 to about 2 wt. %; about 2 to about 12 wt. %, about 2 to about 10 wt. %, about 2 to about 8 wt. %, about 2 to about 6 wt. %, about 2 to about 5 wt. %, about 2 to about 4 wt. %; about 4 to about 12 wt. %, about 4 to about 10 wt. %, about 4 to about 8 wt. %, about 4 to about 6 wt. %, including ranges and subranges therebetween, based on the total weight of the personal care compositions.

Preferably, the fatty alcohol comprises or consists of butyloctanol. In at least one embodiment, the fatty alcohol 2-butyloctanol. Additionally or alternatively, the personal care composition comprises a fatty alcohol selected from decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, and a combination of two or more thereof.

Examples of additional fatty alcohols that may be present in the personal care composition are disclosed below.

The personal care composition may include a saturated or an unsaturated fatty alcohol. Exemplary saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

Exemplary unsaturated liquid fatty alcohol may include in their structure at least one double or triple bond. For example, the fatty alcohols may include several double bonds (such as 2 or 3 double bonds), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

The fatty alcohols may be alkoxylated fatty alcohols, e.g., having about 1 to about 100 moles of an alkylene oxide per mole of alkoxylated fatty alcohol. As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

There personal care composition may comprise fatty alcohol derivatives, such as methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a combination of two or more thereof.

The personal care compositions include a post-biotic blend. The amount of post-biotic blend in the personal care composition may be from about 0.1 to about 7 wt. %, based on the total weight of the personal care composition. For example, the amount of post-biotic blend present in the personal care composition may be from about 0.1 to about 7 wt. %, about 0.1 to about 6 wt. %, about 0.1 to about 5 wt. %, about 0.1 to about 4 wt. %, about 0.1 to about 3.5 wt. %, about 0.1 to about 3 wt. %, about 0.1 to about 2.5 wt. %, about 0.1 to about 2 wt. %, about 0.1 to about 1.5 wt. %, about 0.1 to about 1 wt. %; about 0.25 to about 7 wt. %, about 0.25 to about 6 wt. %, about 0.25 to about 5 wt. %, about 0.25 to about 4 wt. %, about 0.25 to about 3.5 wt. %, about 0.25 to about 3 wt. %, about 0.25 to about 2.5 wt. %, about 0.25 to about 2 wt. %, about 0.25 to about 1.5 wt. %, about 0.25 to about 1 wt. %; about 0.5 to about 7 wt. %, about 0.5 to about 6 wt. %, about 0.5 to about 5 wt. %, about 0.5 to about 4 wt. %, about 0.5 to about 3.5 wt. %, about 0.5 to about 3 wt. %, about 0.5 to about 2.5 wt. %, about 0.5 to about 2 wt. %, about 0.5 to about 1.5 wt. %, about 0.5 to about 1 wt. %; about 0.75 to about 7 wt. %, about 0.75 to about 6 wt. %, about 0.75 to about 5 wt. %, about 0.75 to about 4 wt. %, about 0.75 to about 3.5 wt. %, about 0.75 to about 3 wt. %, about 0.75 to about 2.5 wt. %, about 0.75 to about 2 wt. %, about 0.75 to about 1.5 wt. %; about 1 to about 7 wt. %, about 1 to about 6 wt. %, about 1 to about 5 wt. %, about 1 to about 4 wt. %, about 1 to about 3.5 wt. %, about 1 to about 3 wt. %, about 1 to about 2.5 wt. %, about 1 to about 2 wt. %; about 1.25 to about 7 wt. %, about 1.25 to about 6 wt. %, about 1.25 to about 5 wt. %, about 1.25 to about 4 wt. %, about 1.25 to about 3.5 wt. %, about 1.25 to about 3 wt. %, about 1.25 to about 2.5 wt. %, about 1.25 to about 2 wt. %; about 1.5 to about 7 wt. %, about 1.5 to about 6 wt. %, about 1.5 to about 5 wt. %, about 1.5 to about 4 wt. %, about 1.5 to about 3.5 wt. %, about 1.5 to about 3 wt. %, about 1.5 to about 2.5 wt. %, about 1.5 to about 2 wt. %, including any ranges and subranges therebetween, based on the total weight of the personal care composition.

The post-biotic blend typically includes at least one short chain fatty acid. Short-chain acids are acids with less than six carbon atoms. As used herein short-chain acids mean not only hydrocarbyl acids of formula $C_nH_{2n+1}COOH$, wherein n is 0 to 6, but also short-chained acids that are substituted with oxygen containing groups such as alcohols or oxo groups.

The at least one short chain fatty acid may be selected from pentanoic acid, $CH_3CH_2CH_2CH_2COOH$, isovaleric acid, 3-methylbutanoic acid, $(CH_3)_2CHCH_2COOH$, 2-methylpropanoic acid, $(CH_3)_2CHCOOH$, butanoic acid, $CH_3CH_2CH_2COOH$, $CH_3CH_2COOH$, ethanoic acid, $CH_3COOH$, methanoic acid, $HCOOH$, acetic acid, butanedioic acid, succinic acid, formic acid, propionic acid, butyric acid, isobutyric acid, valeric acid, isovaleric acid, lactic acid, pyruvic acid, a derivative thereof, a salt thereof, and a combination of two or more thereof. Preferably, the post-biotic blend comprises or consists of lactic acid, pyruvic acid, mandelic acid, a salts thereof, and a combination of two or more thereof.

In one embodiment, the post-biotic blend comprises or consists of lactic acid or a salt thereof and comprises pyruvic acid or a salt thereof. The inventors recognized that certain weight ratios of lactic acid and/or salts thereof to pyruvic acid and/or salts thereof may further enhance the growth of desirable bacteria and/or inhibit the growth of undesirable bacteria. For example, the personal care compositions may have lactic acid and/or salts thereof and pyruvic acid and/or salts in a weight ratio of about 6:1 to about 2:1. In some instances, the weight ratio of the weight ratio of lactic acid to pyruvic acid is from about 6:1 to about 2:1, about 5.75:1 to about 2.25:1, about 5.5:1 to about 2.5:1; about 5.25:1 to about 2.75:1, about 5:1 to about 3:1, about 4.75:1 to about 3.25:1, about 4.5:1 to about 3.5:1, or about 4.25:1 to about 3.75:1, including any ranges and subranges therebetween. In one embodiment, the weight ratio of lactic acid to pyruvic acid is about 4:1. In at least one embodiment, the post-biotic blend may be formulated to be a biomimetic blend, e.g., as further discussed below.

The post-biotic blend, in some embodiments, may comprise or consist of the short chain fatty acid(s) further discussed below.

Examples of short-chain acids comprising one carbon include methanoic acid, formic acid, and $HCOOH$. Examples of short-chain acids comprising two carbons include ethanoic acid, acetic acid, $CH_3COOH$, ethanedioic acid, oxalic acid, $HOOCCOOH$, oxoethanoic acid, glyoxylic acid, formylformic acid, $OHCCOOH$, 2-hydroxyethanoic acid, glycolic acid, dicarbonous acid, hydroxyacetic acid, and $HOCH_2COOH$.

Examples of short-chain acids comprising three carbons include propanoic acid, ethanecarboxylic acid, $CH_3CH_2COOH$, prop-2-enoic acid, acrylic acid, acroleic acid, ethylenecarboxylic acid, propene acid, vinylformic acid, $CH_2{=}CH{-}COOH$, 2-propynoic acid, propiolic acid, acetylene carboxylic acid, propargylic acid, $CH{\equiv}C{-}$ COOH, propanedioic acid, malonic acid, methanedicarboxylic acid, HOOC—CH$_2$—COOH, 2-hydroxypropanedioic acid, tartronic acid, hydroxymalonic acid, HOOC—CHOH—COOH, oxopropanedioic acid, mesoxalic acid, ketomalonic acid, HOOC—CO—COOH, 2,2-dihydroxypropanedioic acid, dihydroxymalonic acid, mesoxalic acid monohydrate, HOOC—C(OH)$_2$—COOH, 2-oxopropanoic acid, pyruvic acid, α-ketopropionic acid, acetylformic acid, pyroracemic acid, CH$_3$—CO—COOH, 2-hydroxypropanoic acid, lactic acid, milk acid, CH$_3$—CHOH—COOH, 3-hydroxypropanoic acid, hydracrylic acid, CH$_2$OH—CH$_2$—COOH, 2,3-dihydroxypropanoic acid, glyceric acid, CH$_2$OH—CHOH—COOH, 2-oxiranecarboxylic acid, and glycidic acid.

Examples of short-chain acids comprising four carbons include butanoic acid, butyric acid, propanecarboxylic acid, CH$_3$(CH$_2$)$_2$COOH, 2-methylpropanoic acid, isobutyric acid, isobutanoic acid, (CH$_3$)$_2$CHCOOH, 2-oxobutanoic acid, alpha-ketobutyric acid, CH$_3$—CH$_2$—CO—COOH, 3-oxobutanoic acid, acetoacetic acid, CH$_3$CO—CH$_2$—COOH, 4-oxobutanoic acid, succinic semialdehyde, HC(O)—CH$_2$—CH$_2$—COOH, (E)-butenedioic acid, fumaric acid, trans-1,2-ethylenedicarboxylic acid, 2-butenedioic acid, trans-butenedioic acid, allomaleic acid, boletic acid, donitic acid, lichenic acid, HOOC—CH═CH—COOH, (Z)-butenedioic acid, maleic acid, cis-butenedioic acid, maleinic acid, toxilic acid, HOOC—CH═CH—COOH, oxobutanedioic acid, oxaloacetic acid, oxalacetic acid, oxosuccinic acid, HOOC—CH$_2$—CO—COOH, hydroxybutanedioic acid, malic acid, hydroxybutanedioic acid, HOOC—CH$_2$—CHOH—COOH, 2,3-dihydroxybutanedioic acid, tartaric acid, 2,3-dihydroxysuccinic acid, threaric acid, racemic acid, uvic acid, paratartaric acid, HOOC(CHOH)$_2$COOH, (E)-but-2-enoic acid, crotonic acid, trans-2-butenoic acid, beta-methylacrylic acid, 3-methylacrylic acid, (E)-2-butenoic acid, and CH$_3$—CH═CH—COOH.

Examples of short-chain acids comprising five carbons include pentanoic acid, valeric acid, valerianic acid, butane-1-carboxylic acid, CH$_3$(CH$_2$)$_3$COOH, 3-methylbutanoic acid, iso-valeric acid, (CH$_3$)$_2$CH—CH$_2$—COOH, pentanedioic acid, glutaric acid, propane-1,3-dicarboxylic acid, 1,3-propanedicarboxylic acid, n-pyrotartaric acid, HOOC—(CH$_2$)$_3$—COOH, 2-oxopentanedioic acid, alpha-ketoglutaric acid, 2-ketoglutaric acid, α-ketoglutaric acid, 2-oxoglutaric acid, oxoglutaric acid, and HOOC—(CH$_2$)$_2$—CO—COOH.

Under one embodiment, the biomimetic blend also comprises a short chain alcohol. Examples of a short chain alcohol includes methanol, CH$_3$OH, ethanol, CH$_3$CH$_2$OH, n-propanol, 1-propanol, CH$_3$—CH$_2$—CH$_2$—OH, iso-propanol, 2-propanol, (CH$_3$)$_2$CH—OH, n-butanol, 1-bunatol, CH$_3$—CH$_2$—CH$_2$—CH$_2$—OH, sec-butanol, 2-butanol, CH$_3$—CH$_2$—CHOH—CH$_3$, iso-butanol, (CH$_3$)$_2$CH—CH$_2$—OH, tert-butanol, (CH$_3$)$_3$C—OH, normal amyl alcohol, pentan-1-ol, CH$_3$—(CH$_2$)$_4$OH, isobutyl carbinol, 3-methylbutan-1-ol, isoamyl alcohol, isopentyl alcohol, (CH$_3$)$_2$CH—CH$_2$—CH$_2$—OH, active amyl alcohol, 2-methylbutan-1-ol, CH$_3$—CH$_2$—C(CH$_3$)H—CH$_2$—OH, tertiary butyl carbinol, 2,2-dimethylpropan-1-ol, neopentyl alcohol, (CH$_3$)$_3$C—CH$_2$—OH, 3-pentanol, pentan-3-ol, (CH$_3$—CH$_2$)CH—OH, methylpropyl carbinol, pentan-2-ol, CH$_3$—CH$_2$—CH$_2$—CH(OH)—CH$_3$, methyl isopropyl carbinol, 3-methylbutan-2-ol, (CH$_3$)$_2$CH—C(OH)—CH$_3$, dimethyl ethyl carbinol, 2-methylbutan-2-ol, tertiary amyl alcohol, CH$_3$—CH$_2$—C(CH$_3$)$_2$—OH.

In some embodiments, the biomimetic blend also comprises a short chain polyol. A polyol is an organic compound containing multiple hydroxyl groups. Examples of polyols include a diol, a triol, and a tetrol. An example of a triol is a glycerol.

Lactic acid is a carboxylic acid with the formula CH3-CH(OH)—COOH. Under one embodiment, the lactic acid is L-(+)-lactic acid or (S)-lactic acid. Under another embodiment the lactic acid is D-(-)-lactic acid of (R)-lactic acid. Under yet another embodiment the lactic acid is a mixture of the two stereoisomers.

Under one embodiment, the personal care composition comprises about 0.1 wt. % to about 0.3 wt. % of the biomimetic blend, based on the total weight of the personal care composition. Under one embodiment, the personal care composition comprises about 0.1 wt. % to about 0.5 wt. % of the biomimetic blend, based on the total weight of the personal care composition. Under one embodiment, the personal care composition comprises about 0.1 wt. % to about 0.7 wt. % of the biomimetic blend, based on the total weight of the personal care composition. Under one embodiment, the personal care composition comprises about 0.1 wt. % to about 1.1 wt. % of the biomimetic blend, based on the total weight of the personal care composition. Under one embodiment, the personal care composition comprises about 0.1 wt. % to about 1.3 wt. % of the biomimetic blend, based on the total weight of the personal care composition. Under one embodiment, the personal care composition comprises about 0.1 wt. % to about 1.5 wt. % of the biomimetic blend, based on the total weight of the personal care composition. Under one embodiment, the personal care composition comprises about 0.1 wt. % to about 1.7 wt. % of the biomimetic blend, based on the total weight of the personal care composition.

Under one embodiment, the personal care composition comprises about 0.3 wt. % to about 0.5 wt. % of the biomimetic blend, based on the total weight of the personal care composition. Under one embodiment, the personal care composition comprises about 0.3 wt. % to about 0.7 wt. % of the biomimetic blend, based on the total weight of the personal care composition. Under one embodiment, the personal care composition comprises about 0.3 wt. % to about 1.1 wt. % of the biomimetic blend, based on the total weight of the personal care composition. Under one embodiment, the personal care composition comprises about 0.3 wt. % to about 1.3 wt. % of the biomimetic blend, based on the total weight of the personal care composition. Under one embodiment, the personal care composition comprises about 0.3 wt. % to about 1.5 wt. % of the biomimetic blend, based on the total weight of the personal care composition. Under one embodiment, the personal care composition comprises about 0.3 wt. % to about 1.7 wt. % of the biomimetic blend, based on the total weight of the personal care composition. Under one embodiment, the personal care composition comprises about 0.3 wt. % to about 2.0 wt. % of the biomimetic blend, based on the total weight of the personal care composition.

Under one embodiment, the personal care composition comprises about 0.5 wt. % to about 0.7 wt. % of the biomimetic blend, based on the total weight of the personal care composition. Under one embodiment, the personal care composition comprises about 0.5 wt. % to about 1.1 wt. % of the biomimetic blend, based on the total weight of the personal care composition. Under one embodiment, the personal care composition comprises about 0.5 wt. % to about 1.3 wt. % of the biomimetic blend, based on the total weight of the personal care composition. Under one embodiment, the personal care composition comprises about 0.5 wt. % to about 1.5 wt. % of the biomimetic blend, based on the total weight of the personal care composition. Under one embodiment, the personal care composition comprises about 0.5 wt. % to about 1.7 wt. % of the biomimetic blend, based on the total weight of the personal care composition. Under one embodiment, the personal care composition comprises about 0.5 wt. % to about 2.0 wt. % of the biomimetic blend, based on the total weight of the personal care composition.

Under one embodiment, the personal care composition comprises about 0.7 wt. % to about 1.1 wt. % of the biomimetic blend, based on the total weight of the personal care composition. Under one embodiment, the personal care composition comprises about 0.7 wt. % to about 1.3 wt. % of the biomimetic blend, based on the total weight of the personal care composition. Under one embodiment, the personal care composition comprises about 0.7 wt. % to about 1.5 wt. % of the biomimetic blend, based on the total weight of the personal care composition. Under one embodiment, the personal care composition comprises about 0.7 wt. % to about 1.7 wt. % of the biomimetic blend, based on the total weight of the personal care composition. Under one embodiment, the personal care composition comprises about 0.7 wt. % to about 2.0 wt. % of the biomimetic blend, based on the total weight of the personal care composition.

Under one embodiment, the personal care composition comprises about 0.9 wt. % to about 1.1 wt. % of the biomimetic blend, based on the total weight of the personal care composition. Under one embodiment, the personal care composition comprises about 0.9 wt. % to about 1.3 wt. % of the biomimetic blend, based on the total weight of the personal care composition. Under one embodiment, the personal care composition comprises about 0.9 wt. % to about 1.5 wt. % of the biomimetic blend, based on the total weight of the personal care composition. Under one embodiment, the personal care composition comprises about 0.9 wt. % to about 1.7 wt. % of the biomimetic blend, based on the total weight of the personal care composition. Under one embodiment, the personal care composition comprises about 0.9 wt. % to about 2.0 wt. % of the biomimetic blend, based on the total weight of the personal care composition.

Under one embodiment, the personal care composition comprises about 1.1 wt. % to about 1.3 wt. % of the biomimetic blend, based on the total weight of the personal care composition. Under one embodiment, the personal care composition comprises about 1.1 wt. % to about 1.5 wt. % of the biomimetic blend, based on the total weight of the personal care composition. Under one embodiment, the personal care composition comprises about 1.1 wt. % to about 1.7 wt. % of the biomimetic blend, based on the total weight of the personal care composition. Under one embodiment, the personal care composition comprises about 1.1 wt. % to about 2.0 wt. % of the biomimetic blend, based on the total weight of the personal care composition.

Under one embodiment, the personal care composition comprises about 1.3 wt. % to about 1.5 wt. % of the biomimetic blend, based on the total weight of the personal care composition. Under one embodiment, the personal care composition comprises about 1.3 wt. % to about 1.7 wt. % of the biomimetic blend, based on the total weight of the personal care composition. Under one embodiment, the personal care composition comprises about 1.3 wt. % to about 2.0 wt. % of the biomimetic blend, based on the total weight of the personal care composition. Under one embodiment, the personal care composition comprises about 1.5 wt. % to about 1.7 wt. % of the biomimetic blend, based on the total weight of the personal care composition. Under one embodiment, the personal care composition comprises about 1.5 wt. % to about 2.0 wt. % of the biomimetic blend, based on the total weight of the personal care composition. Under one embodiment, the personal care composition comprises about 1.7 wt. % to about 2.0 wt. % of the biomimetic blend, based on the total weight of the personal care composition.

Under one embodiment, the personal care product of the present invention comprises a biomimetic blend of short chain acids, wherein the short chain are lactic acid, acetic acid, and pyruvic acid. The lactic is the major component, and the pyruvic acid is the smallest component. Under one embodiment, the biomimetic blend comprises about 8 to about 14 parts by weight lactic acid, about 4 to about 6 parts by weight acetic acid, and about 2 to about 3 parts by weight pyruvic acid. The phrase "parts by weight" refers to the weight ratios of the component short chain acids.

Under one embodiment, the biomimetic blend comprises about 8 to about 10 parts by weight lactic acid, about 4 to about 5 parts by weight acetic acid, and about 2.0 to about 2.5 parts by weight pyruvic acid. Under one embodiment, the biomimetic blend comprises about 8 to about 12 parts by weight lactic acid, about 4 to about 5 parts by weight acetic acid, and about 2.0 to about 2.5 parts by weight pyruvic acid. Under one embodiment, the biomimetic blend comprises about 8 to about 14 parts by weight lactic acid, about 4 to about 5 parts by weight acetic acid, and about 2.0 to about 2.5 parts by weight pyruvic acid. Under one embodiment, the biomimetic blend comprises about 10 to about 12 parts by weight lactic acid, about 4 to about 5 parts by weight acetic acid, and about 2.0 to about 2.5 parts by weight pyruvic acid. Under one embodiment, the biomimetic blend comprises about 10 to about 14 parts by weight lactic acid, about 4 to about 5 parts by weight acetic acid, and about 2.0 to about 2.5 parts by weight pyruvic acid. Under one embodiment, the biomimetic blend comprises about 12 to about 14 parts by weight lactic acid, about 4 to about 5 parts by weight acetic acid, and about 2.0 to about 2.5 parts by weight pyruvic acid.

Under one embodiment, the biomimetic blend comprises about 8 to about 10 parts by weight lactic acid, about 4 to about 6 parts by weight acetic acid, and about 2.0 to about 2.5 parts by weight pyruvic acid. Under one embodiment, the biomimetic blend comprises about 8 to about 12 parts by weight lactic acid, about 4 to about 6 parts by weight acetic acid, and about 2.0 to about 2.5 parts by weight pyruvic acid. Under one embodiment, the biomimetic blend comprises about 8 to about 14 parts by weight lactic acid, about 4 to about 6 parts by weight acetic acid, and about 2.0 to about 2.5 parts by weight pyruvic acid. Under one embodiment, the biomimetic blend comprises about 10 to about 12 parts by weight lactic acid, about 4 to about 6 parts by weight acetic acid, and about 2.0 to about 2.5 parts by weight pyruvic acid. Under one embodiment, the biomimetic blend comprises about 10 to about 14 parts by weight lactic acid, about 4 to about 6 parts by weight acetic acid, and about 2.0 to about 2.5 parts by weight pyruvic acid. Under one embodiment, the biomimetic blend comprises about 12 to about 14 parts by weight lactic acid, about 4 to about 6 parts by weight acetic acid, and about 2.0 to about 2.5 parts by weight pyruvic acid.

Under one embodiment, the biomimetic blend comprises about 8 to about 10 parts by weight lactic acid, about 5 to about 6 parts by weight acetic acid, and about 2.0 to about 2.5 parts by weight pyruvic acid. Under one embodiment, the biomimetic blend comprises about 8 to about 12 parts by weight lactic acid, about 5 to about 6 parts by weight acetic acid, and about 2.0 to about 2.5 parts by weight pyruvic acid.

Under one embodiment, the biomimetic blend comprises about 8 to about 14 parts by weight lactic acid, about 5 to about 6 parts by weight acetic acid, and about 2.0 to about 2.5 parts by weight pyruvic acid. Under one embodiment, the biomimetic blend comprises about 10 to about 12 parts by weight lactic acid, about 5 to about 6 parts by weight acetic acid, and about 2.0 to about 2.5 parts by weight pyruvic acid. Under one embodiment, the biomimetic blend comprises about 10 to about 14 parts by weight lactic acid, about 5 to about 6 parts by weight acetic acid, and about 2.0 to about 2.5 parts by weight pyruvic acid. Under one embodiment, the biomimetic blend comprises about 12 to about 14 parts by weight lactic acid, about 5 to about 6 parts by weight acetic acid, and about 2.0 to about 2.5 parts by weight pyruvic acid.

Under one embodiment, the biomimetic blend comprises about 8 to about 10 parts by weight lactic acid, about 4 to about 5 parts by weight acetic acid, and about 2.0 to about 3.0 parts by weight pyruvic acid. Under one embodiment, the biomimetic blend comprises about 8 to about 12 parts by weight lactic acid, about 4 to about 5 parts by weight acetic acid, and about 2.0 to about 3.0 parts by weight pyruvic acid. Under one embodiment, the biomimetic blend comprises about 8 to about 14 parts by weight lactic acid, about 4 to about 5 parts by weight acetic acid, and about 2.0 to about 3.0 parts by weight pyruvic acid. Under one embodiment, the biomimetic blend comprises about 10 to about 12 parts by weight lactic acid, about 4 to about 5 parts by weight acetic acid, and about 2.0 to about 3.0 parts by weight pyruvic acid. Under one embodiment, the biomimetic blend comprises about 10 to about 14 parts by weight lactic acid, about 4 to about 5 parts by weight acetic acid, and about 2.0 to about 3.0 parts by weight pyruvic acid. Under one embodiment, the biomimetic blend comprises about 12 to about 14 parts by weight lactic acid, about 4 to about 5 parts by weight acetic acid, and about 2.0 to about 3.0 parts by weight pyruvic acid.

Under one embodiment, the biomimetic blend comprises about 8 to about 10 parts by weight lactic acid, about 4 to about 6 parts by weight acetic acid, and about 2.0 to about 3.0 parts by weight pyruvic acid. Under one embodiment, the biomimetic blend comprises about 8 to about 12 parts by weight lactic acid, about 4 to about 6 parts by weight acetic acid, and about 2.0 to about 3.0 parts by weight pyruvic acid. Under one embodiment, the biomimetic blend comprises about 8 to about 14 parts by weight lactic acid, about 4 to about 6 parts by weight acetic acid, and about 2.0 to about 3.0 parts by weight pyruvic acid. Under one embodiment, the biomimetic blend comprises about 10 to about 12 parts by weight lactic acid, about 4 to about 6 parts by weight acetic acid, and about 2.0 to about 3.0 parts by weight pyruvic acid. Under one embodiment, the biomimetic blend comprises about 10 to about 14 parts by weight lactic acid, about 4 to about 6 parts by weight acetic acid, and about 2.0 to about 3.0 parts by weight pyruvic acid. Under one embodiment, the biomimetic blend comprises about 12 to about 14 parts by weight lactic acid, about 4 to about 6 parts by weight acetic acid, and about 2.0 to about 3.0 parts by weight pyruvic acid.

Under one embodiment, the biomimetic blend comprises about 8 to about 10 parts by weight lactic acid, about 5 to about 6 parts by weight acetic acid, and about 2.0 to about 3.0 parts by weight pyruvic acid. Under one embodiment, the biomimetic blend comprises about 8 to about 12 parts by weight lactic acid, about 5 to about 6 parts by weight acetic acid, and about 2.0 to about 3.0 parts by weight pyruvic acid. Under one embodiment, the biomimetic blend comprises about 8 to about 14 parts by weight lactic acid, about 5 to about 6 parts by weight acetic acid, and about 2.0 to about 3.0 parts by weight pyruvic acid. Under one embodiment, the biomimetic blend comprises about 10 to about 12 parts by weight lactic acid, about 5 to about 6 parts by weight acetic acid, and about 2.0 to about 3.0 parts by weight pyruvic acid. Under one embodiment, the biomimetic blend comprises about 10 to about 14 parts by weight lactic acid, about 5 to about 6 parts by weight acetic acid, and about 2.0 to about 3.0 parts by weight pyruvic acid. Under one embodiment, the biomimetic blend comprises about 12 to about 14 parts by weight lactic acid, about 5 to about 6 parts by weight acetic acid, and about 2.0 to about 3.0 parts by weight pyruvic acid.

Under one embodiment, the biomimetic blend comprises about 8 to about 10 parts by weight lactic acid, about 4 to about 5 parts by weight acetic acid, and about 2.5 to about 3.0 parts by weight pyruvic acid. Under one embodiment, the biomimetic blend comprises about 8 to about 12 parts by weight lactic acid, about 4 to about 5 parts by weight acetic acid, and about 2.5 to about 3.0 parts by weight pyruvic acid. Under one embodiment, the biomimetic blend comprises about 8 to about 14 parts by weight lactic acid, about 4 to about 5 parts by weight acetic acid, and about 2.5 to about 3.0 parts by weight pyruvic acid. Under one embodiment, the biomimetic blend comprises about 10 to about 12 parts by weight lactic acid, about 4 to about 5 parts by weight acetic acid, and about 2.5 to about 3.0 parts by weight pyruvic acid. Under one embodiment, the biomimetic blend comprises about 10 to about 14 parts by weight lactic acid, about 4 to about 5 parts by weight acetic acid, and about 2.5 to about 3.0 parts by weight pyruvic acid. Under one embodiment, the biomimetic blend comprises about 12 to about 14 parts by weight lactic acid, about 4 to about 5 parts by weight acetic acid, and about 2.5 to about 3.0 parts by weight pyruvic acid.

Under one embodiment, the biomimetic blend comprises about 8 to about 10 parts by weight lactic acid, about 4 to about 6 parts by weight acetic acid, and about 2.5 to about 3.0 parts by weight pyruvic acid. Under one embodiment, the biomimetic blend comprises about 8 to about 12 parts by weight lactic acid, about 4 to about 6 parts by weight acetic acid, and about 2.5 to about 3.0 parts by weight pyruvic acid. Under one embodiment, the biomimetic blend comprises about 8 to about 14 parts by weight lactic acid, about 4 to about 6 parts by weight acetic acid, and about 2.5 to about 3.0 parts by weight pyruvic acid. Under one embodiment, the biomimetic blend comprises about 10 to about 12 parts by weight lactic acid, about 4 to about 6 parts by weight acetic acid, and about 2.5 to about 3.0 parts by weight pyruvic acid. Under one embodiment, the biomimetic blend comprises about 10 to about 14 parts by weight lactic acid, about 4 to about 6 parts by weight acetic acid, and about 2.5 to about 3.0 parts by weight pyruvic acid. Under one embodiment, the biomimetic blend comprises about 12 to about 14 parts by weight lactic acid, about 4 to about 6 parts by weight acetic acid, and about 2.5 to about 3.0 parts by weight pyruvic acid.

Under one embodiment, the biomimetic blend comprises about 8 to about 10 parts by weight lactic acid, about 5 to about 6 parts by weight acetic acid, and about 2.5 to about 3.0 parts by weight pyruvic acid. Under one embodiment, the biomimetic blend comprises about 8 to about 12 parts by weight lactic acid, about 5 to about 6 parts by weight acetic acid, and about 2.5 to about 3.0 parts by weight pyruvic acid. Under one embodiment, the biomimetic blend comprises about 8 to about 14 parts by weight lactic acid, about 5 to about 6 parts by weight acetic acid, and about 2.5 to about 3.0 parts by weight pyruvic acid. Under one embodiment, the biomimetic blend comprises about 10 to about 12 parts by weight lactic acid, about 5 to about 6 parts by weight acetic acid, and about 2.5 to about 3.0 parts by weight pyruvic acid. Under one embodiment, the biomimetic blend comprises about 10 to about 14 parts by weight lactic acid, about 5 to about 6 parts by weight acetic acid, and about 2.5 to about 3.0 parts by weight pyruvic acid. Under one embodiment, the biomimetic blend comprises about 12 to about 14 parts by weight lactic acid, about 5 to about 6 parts by weight acetic acid, and about 2.5 to about 3.0 parts by weight pyruvic acid.

Under one embodiment, the biomimetic blend comprises about 8 to about 14 parts by weight lactic acid, about 4 to about 6 parts by weight acetic acid, and about 2.0 to about 3.0 parts by weight pyruvic acid, and about 1 part of glycerol.

The personal care compositions may include ethylhexylglycerin in an amount that may vary, but typically ranges from about 0.1 to about 2 wt. %, based on the total weight of the personal care composition. For example, the amount of ethylhexylglycerin in the personal care composition may be from about 0.1 to about 2 wt. %, about 0.1 to about 1.8 wt. %, about 0.1 to about 1.6 wt. %, about 0.1 to about 1.4 wt. %, about 0.1 to about 1.2 wt. %, about 0.1 to about 1 wt. %, about 0.1 to about 0.8 wt. %, about 0.1 to about 0.7 wt. %, about 0.1 to about 0.6 wt. %, about 0.1 to about 0.5 wt. %, about 0.1 to about 0.4 wt. %, about 0.1 to about 0.3 wt. %, about 0.1 to about 0.2 wt. %; from about 0.2 to about 2 wt. %, about 0.2 to about 1.8 wt. %, about 0.2 to about 1.6 wt. %, about 0.2 to about 1.4 wt. %, about 0.2 to about 1.2 wt. %, about 0.2 to about 1 wt. %, about 0.2 to about 0.8 wt. %, about 0.2 to about 0.7 wt. %, about 0.2 to about 0.6 wt. %, about 0.2 to about 0.5 wt. %, about 0.2 to about 0.4 wt. %, about 0.2 to about 0.3 wt. %; from about 0.3 to about 2 wt. %, about 0.3 to about 1.8 wt. %, about 0.3 to about 1.6 wt. %, about 0.3 to about 1.4 wt. %, about 0.3 to about 1.2 wt. %, about 0.3 to about 1 wt. %, about 0.3 to about 0.8 wt. %, about 0.3 to about 0.7 wt. %, about 0.3 to about 0.6 wt. %; from about 0.4 to about 2 wt. %, about 0.4 to about 1.8 wt. %, about 0.4 to about 1.6 wt. %, about 0.4 to about 1.4 wt. %, about 0.4 to about 1.2 wt. %, about 0.4 to about 1 wt. %, about 0.4 to about 0.8 wt. %, about 0.4 to about 0.7 wt. %; from about 0.5 to about 2 wt. %, about 0.5 to about 1.8 wt. %, about 0.5 to about 1.6 wt. %, about 0.5 to about 1.4 wt. %, about 0.5 to about 1.2 wt. %, about 0.5 to about 1 wt. %, about 0.5 to about 0.8 wt. %; from about 0.7 to about 2 wt. %, about 0.7 to about 1.8 wt. %, about 0.7 to about 1.6 wt. %, about 0.7 to about 1.4 wt. %, about 0.7 to about 1.2 wt. %, about 0.7 to about 1 wt. %; about 0.9 to about 2 wt. %, about 0.9 to about 1.8 wt. %, about 0.9 to about 1.6 wt. %, about 0.9 to about 1.4 wt. %, about 0.9 to about 1.2 wt. %; about 1.2 to about 2 wt. %, about 1.2 to about 1.8 wt. %, about 1.2 to about 1.6 wt. %; from about 1.5 to about 2 wt. %, about 1.5 to about 1.8 wt. %; from about 1.7 to about 2, or any range or subrange thereof, based on the total weight of the personal care composition.

The personal care composition may include one or more polyol(s). The polyol(s) may be chosen from glycols or compounds with numerous hydroxyl groups. In some cases, the one or more polyols is/are selected from the group consisting of $C_2$-$C_{32}$ polyols. The one or more polyols may be liquid at ambient temperature (25° C.). The one or more polyols may have from 2 to 32 carbon atoms, from 3 to 16 carbon atoms, or from 3 to 12 carbon atoms.

Polyols that may be included in the hair care composition, in certain instances, include ethylene glycol, propylene glycol, butylene glycol, hexylene glycol, glycerin, diglycerin, diethylene glycol, and dipropylene glycol, and mixtures thereof. In some cases, the polyol is propylene glycol. In some further cases, the polyol is one or both of propylene glycol and butylene glycol. Additionally, in some cases, the hair care composition comprises at least propylene glycol, and optionally one or more polyols other than propylene glycol.

Non-limiting examples of polyols that may, optionally, be included in the hair care include and/or may be chosen from alkanediols such as glycerin, 1,2,6-hexanetriol, trimethylolpropane, ethylene glycol, propylene glycol, butylene glycol, pentylene glycol, hexylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, sorbitol, sorbitan, triacetin, and a mixture thereof.

The one or more polyols may, optionally, be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol. In some cases, the one or more polyols may include or are chosen from ethylene glycol, propylene glycol, butylene glycol, hexylene glycol, pentylene glycol, 1,3-propanediol, diethylene glycol, dipropylene glycol, 1,4-butanediol, 1,5-pentanediol, hexane-1,6-diol, glycerin, diglycerin, caprylyl glycol, and a mixture thereof.

In certain embodiments, the personal care composition may include polyol(s) selected from glycerin (preferably, vegetable refined glycerin), butylene glycol, and 1,3-propanediol, polyglutamic acid, saccharide isomerate, and combinations thereof. In some embodiments, the polyol is a polyethylene glycol, such as polyethylene glycol 600 (CAS-25322-68-3).

The one or more polyol(s) may be present in the personal care composition in an amount that may vary depending on the form of personal care composition. For example, the personal care composition may have polyol(s) in an amount ranging from about 5 to about 30%, based on the total weight of the personal care composition. For example, the amount of humectant or hygroscopic agent present in the personal care compositions may be from about 5 to about 30 wt. %, about 5 to about 25 wt. %, about 5 to about 22 wt. %, about 5 to about 20 wt. %, about 5 to about 18 wt. %, about 5 to about 16 wt. %; from about 8 to about 30 wt. %, about 8 to about 25 wt. %, about 8 to about 22 wt. %, about 8 to about 20 wt. %, about 8 to about 18 wt. %, about 8 to about 16 wt. %; from about 10 to about 30 wt. %, about 10 to about 25 wt. %, about 10 to about 22 wt. %, about 10 to about 20 wt. %, about 10 to about 18 wt. %, about 10 to about 16 wt. %; from about 12 to about 30 wt. %, about 12 to about 25 wt. %, about 12 to about 22 wt. %, about 12 to about 20 wt. %, about 12 to about 18 wt. %, about 12 to about 16 wt. %; from about 14 to about 30 wt. %, about 14 to about 25 wt. %, about 14 to about 22 wt. %, about 14 to about 20 wt. %, about 14 to about 18 wt. %, about 14 to about 16 wt. %, including ranges and subranges thereof, based on the total weight of the personal care composition. In at least one embodiment, the personal care composition is in the form of a deodorant and/or antiperspirant and has one or more polyol(s) present in an amount from about 5 to about 30 wt. % or any of the amounts discussed in this paragraph, based on the total weight of the personal care composition.

The personal care compositions may comprise one or more thickeners. The thickeners may be chosen from polysaccharides; carboxylic acid polymers; crosslinked polyacrylate polymers; polyacrylamide polymers; gums, and combinations of two or more thereof. Examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof.

Non-limiting examples of carboxylic acid polymers include crosslinked carboxylic acid polymers containing one or more monomers derived from acrylic acid, substituted acrylic acids, and salts and esters of these acrylic acids and the substituted acrylic acids, such as carbomers. Non-limiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, sodium carrageenan, tragacanth gum, xanthan gum, and mixtures thereof.

In certain cases, the personal care composition may be formulated to have thickening polymers, such as polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (e.g., carboxymethyl cellulose, methyl cellulose, methylhydroxypropyl cellulose, hydroxyethyl cellulose, hydroxypropyl cellulose, cellulose sulfate sodium salt), and/or starch derivatives (e.g., starch oxide, dialdehyde starch, dextrin, British gum, acetyl starch, starch phosphate, carboxymethyl starch, hydroxyethyl starch, hydroxypropyl starch). In some embodiments, the thickeners are selected from among hydroxypropyl methylcellulose, polyethylene glycols (PEGs), polyacrylic acids, cross-linked homopolymer of acrylic acid, and acrylates of $C_{10-30}$ alkyl acrylate crosspolymer.

The personal care composition may, in certain embodiments, comprise a surfactant. The surfactant can be any anionic, nonionic, amphoteric, or zwitterionic surfactant, or combinations thereof. The amount of surfactant(s) in the composition may be about 1 to about 25 wt. %, based on the total weight of the personal care composition. In some instances, the amount of surfactant(s) present in the personal care composition is about 1 to about 25 wt. %, about 2 to about 25 wt. %, about 3 to about 25 wt. %, about 4 to about 25 wt. %, about 5 to about 25 wt. %, about 7.5 to about 25 wt. %, about 10 to about 25 wt. %, about 15 to about 25 wt. %, about 20 to about 25 wt. %; about 1 to about 20 wt. %, about 2 to about 20 wt. %, about 3 to about 20 wt. %, about 4 to about 20 wt. %, about 5 to about 20 wt. %, about 7.5 to about 20 wt. %, about 10 to about 20 wt. %, about 15 to about 20 wt. %; about 1 to about 15 wt. %, about 2 to about 15 wt. %, about 3 to about 15 wt. %, about 4 to about 15 wt. %, about 5 to about 15 wt. %, about 7.5 to about 15 wt. %, about 10 to about 15 wt. %; about 1 to about 10 wt. %, about 2 to about 10 wt. %, about 3 to about 10 wt. %, about 4 to about 10 wt. %, about 5 to about 10 wt. %, about 7.5 to about 10 wt. %; about 1 to about 7.5 wt. %, about 2 to about 7.5 wt. %, about 3 to about 7.5 wt. %, about 4 to about 7.5 wt. %, about 5 to about 7.5 wt. %; about 1 to about 5 wt. %, about 2 to about 5 wt. %, about 3 to about 5 wt. %, about 4 to about 5 wt. %; about 1 to about 4 wt. %, about 2 to about 4 wt. %, about 3 to about 4 wt. %, including all ranges and subranges therebetween, based on the total weight of the personal care composition.

Under an embodiment, multiple surfactants are used to achieve desired product qualities. A primary surfactant provides good foaming ability and cleaning effectiveness, while a secondary surfactant adds qualities of mildness to prevent irritation or over-drying of the skin. To prevent ingredients from separating, emulsifiers such as diethanolamine may be added. Additional ingredients include conditioning agents that moisturize the skin during and after product use. Ingredients, like scent in the form of essential oils or fragrance oils, and colorant in the form of water soluble dyes may also be used.

A variety of anionic surfactants can be utilized in the personal care composition including, for example, long chain alkyl ($C_6$-$C_{22}$) materials such as long chain alkyl sulfates, long chain alkyl sulfonates, long chain alkyl phosphates, long chain alkyl ether sulfates, long chain alkyl alpha olefin sulfonates, long chain alkyl taurates, long chain alkyl isethionates (SCI), long chain alkyl glyceryl ether sulfonates (AGES), sulfosuccinates and the like. These anionic surfactants can be alkoxylated, for example, ethoxylated, although alkoxylation is not required. These surfactants are typically highly water soluble as their sodium, potassium, alkyl and ammonium or alkanol ammonium containing salt form and can provide high foaming cleansing power. Other equivalent anionic surfactants may be used. In one embodiment, the anionic surfactant comprises sodium laureth sulfate, sodium pareth sulfate, and combinations thereof. Anionic surfactants can be included in any desired amount.

In one embodiment, anionic surfactants are present in the personal care composition in an amount of 0 to about 15 wt. %, based on the total weight of the personal care composition. For example, the anionic surfactants may be present in the personal care composition in an amount from about 0.5 to about 15 wt. %, about 0.5 to about 12 wt. %, about 0.5 to about 10 wt. %, about 0.5 to about 8 wt. %, about 0.5 to about 6 wt. %, about 0.5 to about 4 wt. %, about 0.5 to about 2 wt. %, about 0.5 to about 1 wt. %; from about 1 to about 15 wt. %, about 1 to about 12 wt. %, about 1 to about 10 wt. %, about 1 to about 8 wt. %, about 1 to about 6 wt. %, about to about 4 wt. %, about 1 to about 2 wt. %; from about 2 to about 15 wt. %, about 2 to about 12 wt. %, about 2 to about 10 wt. %, about 2 to about 8 wt. %, about 2 to about 6 wt. %, about 2 to about 4 wt. %; from about 4 to about 15 wt.

%, about 4 to about 12 wt. %, about 4 to about 10 wt. %, about 4 to about 8 wt. %, about 4 to about 6 wt. %; from about 6 to about 15 wt. %, about 6 to about 12 wt. %, about 6 to about 10 wt. %, about 6 to about 8 wt. %; from about 8 to about 15 wt. %, about 8 to about 12 wt. %, about 8 to 10 wt. %, or any range or subrange thereof, based on the total weight of the personal care composition. In one embodiment, anionic surfactants are present in an amount of about 6 to about 8 wt. %, based on the total weight of the personal care composition.

Amphoteric surfactants may also be included in the composition. These surfactants are typically characterized by a combination of high surfactant activity, lather forming and mildness. Amphoteric surfactants include, but are not limited to derivatives of aliphatic secondary and tertiary amines in which the aliphatic radical can be straight chain or branched and wherein one of the aliphatic substituents contains about 8 to about 18 carbon atoms and one contains an anionic water solubilizing group, e.g., carboxy, sulfonate, sulfate, phosphate, or phosphonate. Examples of such compounds include sodium 3-dodecyaminopropionate, sodium 3-dodecylaminopropane sulfonate, N-alkyl taurines and N-higher alkyl aspartic acids. Other equivalent amphoteric surfactants may be used. Examples of amphoteric surfactants include, but are not limited to, a range of betaines including, for example, high alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, and lauryl bis-(2-hydroxypropyl)alpha-carboxyethyl betaine, sulfobetaines such as coco dimethyl sulfopropyl betaine, stearyl dimethyl sulfopropyl betaine, amido betaines, amidosulfobetaines and the like. Betaines having a long chain alkyl group, particularly coco, may be particularly useful as are those that include an amido groups such as the cocamidopropyl and cocoamidoethyl betaines.

Amphoteric surfactants can be included in any desired amount. In one embodiment, amphoteric surfactants are present in the composition in an amount of 0 to about 15 wt. %, based on the total weight of the personal care composition. For example, the amphoteric surfactants may be present in the personal care composition in an amount from about 0.5 to about 15 wt. %, about 0.5 to about 12 wt. %, about 0.5 to about 10 wt. %, about 0.5 to about 8 wt. %, about 0.5 to about 6 wt. %, about 0.5 to about 4 wt. %, about 0.5 to about 2 wt. %, about 0.5 to about 1 wt. %; from about 1 to about 15 wt. %, about 1 to about 12 wt. %, about 1 to about 10 wt. %, about 1 to about 8 wt. %, about 1 to about 6 wt. %, about to about 4 wt. %, about 1 to about 2 wt. %; from about 2 to about 15 wt. %, about 2 to about 12 wt. %, about 2 to about 10 wt. %, about 2 to about 8 wt. %, about 2 to about 6 wt. %, about 2 to about 4 wt. %; from about 4 to about 15 wt. %, about 4 to about 12 wt. %, about 4 to about 10 wt. %, about 4 to about 8 wt. %, about 4 to about 6 wt. %; from about 6 to about 15 wt. %, about 6 to about 12 wt. %, about 6 to about 10 wt. %, about 6 to about 8 wt. %; from about 8 to about 15 wt. %, about 8 to about 12 wt. %, about 8 to 10 wt. %, or any range or subrange thereof, based on the total weight of the personal care composition. In one embodiment, the amphoteric surfactants are present in the composition in an amount of about 4 to about 6 wt. %, based on the personal care composition.

The personal care composition may include one or more nonionic surfactant(s), Examples of nonionic surfactants include polysorbate 20, long chain alkyl glucosides having $C_8$-$C_{22}$ alkyl groups; coconut fatty acid monoethanolamides such as cocamide MEA; coconut fatty acid diethanolamides, fatty alcohol ethoxylates (alkylpolyethylene glycols); alkylphenol polyethylene glycols; alkyl mercaptan polyethylene glycols; fatty amine ethoxylates (alkylaminopolyethylene glycols); fatty acid ethoxylates (acylpolyethylene glycols); polypropylene glycol ethoxylates (for example the PLURONIC™ block copolymers commercially available from BASF); fatty acid alkylolamides, (fatty acid amide polyethylene glycols); N-alkyl-, N-alkoxypolyhydroxy fatty acid amides; sucrose esters; sorbitol esters; polyglycol ethers; and combinations thereof.

The nonionic surfactant(s) may be selected from secondary alcohol ethoxylates, polyoxyethylene stearyl ethers, polyoxyethylene ethers, and mixtures of two or more thereof. The personal care compositions may include a nonionic surfactant blend including two or more fatty alcohol ethoxylates, each having a polyethylene oxide chain length of at least 2. Preferred fatty alcohol ethoxylates generally have a fatty alcohol chain length of $C_{12}$ to $C_{24}$, a degree of unsaturation of 0-2, and a polyethylene oxide chain length of 2 to 150 ethylene oxide units. For example, the fatty alcohol ethoxylates may have the general formula: $CH_3—(CH_2)_x—CH_2—O—(CH_2—CH_2—O—)_yH—$, where X=10-20, Y=2-100. In some cases, the blend of fatty alcohol ethoxylates include at least one fatty alcohol ethoxylate having a long polyethylene oxide chain length and at least one fatty alcohol ethoxylate having a short polyethylene oxide chain length. Suitable long chain length fatty alcohol ethoxylates have a polyethylene oxide chain length greater than 20, preferably 21 to 150, more preferably 21 to 100.

Examples of long chain fatty alcohol ethoxylates include Steareth-100 (100 indicates the polyethylene oxide chain length) and Steareth 21. Other long chain fatty alcohol ethoxylates may be used, e.g., Ceteth-100, Oleth-100 Myreth-100, and Beheneth-100. Examples of short chain length fatty alcohol ethoxylates include those having a polyethylene oxide chain length of less than or equal to 20, preferably 2 to 20. For example, the short chain length fatty alcohol ethoxylates may be selected from Steareth-2, Steareth-10, Ceteth-20, Steareth-20, Myreth-20, Oleth-20 and Beheneth-20.

The non-ionic surfactants may be selected from polyoxyethylene ethers, such as polyoxyethylene stearyl ethers compounds. The polyoxyethylene ethers may comprise a mixture of high molecular mass saturated fatty alcohols, such as cetyl alcohol and stearyl alcohol, and ethylene oxide. The polyoxyethylene ethers may be selected from Ceteareth-2, Ceteareth-3, Ceteareth-4, Ceteareth-5, Ceteareth-6, Ceteareth-7, Ceteareth-8, Ceteareth-9, Ceteareth-10, Ceteareth-11, Ceteareth-12, and a combination of two or more thereof. Examples of polyoxyethylene stearyl ethers compounds include Steareth-2, Steareth-4, Steareth-6, Steareth-7, Steareth-21, Steareth-10, Steareth-11, Steareth-13, Steareth-15, Steareth-20, or combinations of two or more thereof.

Nonionic surfactants can be included in any desired amount. In one embodiment, nonionic surfactants are present in the composition in an amount of 0 to about 3 wt. %, based on the total weight of the personal care composition. In one embodiment, nonionic surfactants are present in the composition in an amount from about 0.5 to about 15 wt. %, about 0.5 to about 12 wt. %, about 0.5 to about 10 wt. %, about 0.5 to about 8 wt. %, about 0.5 to about 6 wt. %, about 0.5 to about 4 wt. %, about 0.5 to about 2 wt. %, about 0.5 to about 1 wt. %; from about 1 to about 15 wt. %, about 1 to about 12 wt. %, about 1 to about 10 wt. %, about 1 to about 8 wt. %, about 1 to about 6 wt. %, about to about 4 wt.

%, about 1 to about 2 wt. %; from about 2 to about 15 wt. %, about 2 to about 12 wt. %, about 2 to about 10 wt. %, about 2 to about 8 wt. %, about 2 to about 6 wt. %, about 2 to about 4 wt. %; from about 4 to about 15 wt. %, about 4 to about 12 wt. %, about 4 to about 10 wt. %, about 4 to about 8 wt. %, about 4 to about 6 wt. %; from about 6 to about 15 wt. %, about 6 to about 12 wt. %, about 6 to about 10 wt. %, about 6 to about 8 wt. %; from about 8 to about 15 wt. %, about 8 to about 12 wt. %, about 8 to 10 wt. %, or any range or subrange thereof, based on the total weight of the personal care composition.

Cationic surfactants can also be included in the composition. Examples of cationic surfactants include any quaternium or polyquaternium compound. Cationic surfactants can be included at any desired level. In one embodiment, cationic surfactants are present in the composition in an amount of 0 to about 2 wt. %, based on the total weight of the personal care composition. For example, the amount of cationic surfactants in the personal care composition may be from about 0.05 to about 2 wt. %, about 0.05 to about 1.8 wt. %, about 0.05 to about 1.6 wt. %, about 0.05 to about 1.4 wt. %, about 0.05 to about 1.2 wt. %, about 0.05 to about 1 wt. %, about 0.05 to about 0.8 wt. %, about 0.05 to about 0.6 wt. %, about 0.05 to about 0.4 wt. %, about 0.05 to about 0.2 wt. %, about 0.05 to about 0.1 wt. %; from about 0.1 to about 2 wt. %, about 0.1 to about 1.8 wt. %, about 0.1 to about 1.6 wt. %, about 0.1 to about 1.4 wt. %, about 0.1 to about 1.2 wt. %, about 0.1 to about 1 wt. %, about 0.1 to about 0.8 wt. %, about 0.1 to about 0.6 wt. %, about 0.1 to about 0.4 wt. %; from about 0.3 to about 2 wt. %, about 0.3 to about 1.8 wt. %, about 0.3 to about 1.6 wt. %, about 0.3 to about 1.4 wt. %, about 0.3 to about 1.2 wt. %, about 0.3 to about 1 wt. %, about 0.3 to about 0.8 wt. %; from about 0.6 to about 2 wt. %, about 0.6 to about 1.8 wt. %, about 0.6 to about 1.6 wt. %, about 0.6 to about 1.4 wt. %, about 0.6 to about 1.2 wt. %, about 0.6 to about 1 wt. %; from about 0.9 to about 2 wt. %, about 0.9 to about 1.8 wt. %, about 0.9 to about 1.6 wt. %, about 0.9 to about 1.4 wt. %; from about 1.2 to about 2 wt. %, about 1.2 to about 1.8 wt. %, about 1.2 to about 1.6 wt. %; from about 1.5 to about 2 wt. %, about 1.5 to about 1.8 wt. %, or any range or subrange thereof, based on the total weight of the personal care composition. In one embodiment, cationic surfactants are present in the composition in an amount of about 0.1 to about 0.3 wt. %, based on the total weight of the personal care composition.

The personal care compositions, in certain embodiments, may further comprise a cationic polymer. The cationic polymers can comprise mixtures of monomer units derived from amine- and/or quaternary ammonium-substituted monomer and/or compatible spacer monomers. Suitable cationic polymers include, for example: copolymers of 1-vinyl-2-pyrrolidine and 1-vinyl-3-methyl-imidazolium salt (e.g., chloride salt) (referred to as Polyquaternium-16) such as those commercially available from BASF under the LUVIQUAT tradename (e.g., LUVIQUAT FC 370); copolymers of 1-vinyl-2-pyrrolidine and dimethylaminoethyl methacrylate (referred to as Polyquaternium-11) such as those commercially from Gar Corporation (Wayne, N.J., USA) under the GAFQUAT tradename (e.g., GAFQUAT 755N); and cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7).

Other cationic polymers that may be used include polysaccharide polymers, such as cationic cellulose derivatives and cationic starch derivatives. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium-24). These materials are available from Amerchol Corp. (Edison, N.J., USA) under the tradename Polymer LM-200. Additionally or alternatively, the cationic conditioning polymers may include or be chosen from cationic guar gum derivatives, such as guar hydroxypropyltrimonium chloride.

The personal care composition may include or be selected from polyquaterniums. In one instance, the one or more cationic polymers is selected from polyquaternium 4, polyquaternium 6, polyquaternium 7, polyquaternium 10, polyquaternium 11, polyquaternium 16, polyquaternium 22, polyquaternium 28, polyquaternium 32, polyquaternium-46, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-63, polyquaternium-64, polyquaternium-65, polyquaternium-66, polyquaternium-67, polyquaternium-70, polyquaternium-73, polyquaternium-74, polyquaternium-75, polyquaternium-76, polyquaternium-77, polyquaternium-78, polyquaternium-79, polyquaternium-80, polyquaternium-81, polyquaternium-82, polyquaternium-84, polyquaternium-85, polyquaternium-86, polyquaternium-87, polyquaternium-90, polyquaternium-91, polyquaternium-92, polyquaternium-94, guar hydroxypropyltrimonium chloride, and a combination of two or more thereof. In at least one embodiment, the cationic polymer comprises a copolymer of acrylamide and diallyldimethylammonium chloride.

Skin and/or hair compatible oils can be included in the composition. Skin and/or hair compatible oils include a range of liquid hydrocarbons, for example, linear and branched oils such as liquid paraffin, squalene, squalane, mineral oil, low viscosity synthetic hydrocarbons such as polyalphaolefins, commercially available from ExxonMobil under the trade name PURESYN PAO and polybutene under the trade name PANALANE™ or INDOPOL™. Light (low viscosity) highly branched hydrocarbon oils may also be suitable in some instances. Other useful skin and/or compatible oils may be silicone based, for example, linear and cyclic polydimethyl siloxane, organo functional silicones (alkyl and alkyl aryl), and amino silicones. In at least one embodiment, the personal care composition includes isododecane.

The personal care composition may include alpha hydroxy acids, beta hydroxy acids, polyhydroxy acids or combinations thereof. For instance, the personal care composition may include one or more one or more alpha hydroxy acid(s), such as those selected from $C_3$ to $C_7$ alpha-hydroxy acid or $C_4$ to $C_6$ alpha-hydroxy acid. The alpha hydroxyl acid may be in the form of a salt, such as a sodium salt or a potassium salt. In at least one embodiment, the salt is a sodium salt (i.e., the cation associated with the salt is a sodium). Non-limiting examples of alpha hydroxy acids include, but are not limited to, mandelic acid, glycolic acid, citric acid, lactic acid, malic acid, tartaric acid, phytic acid, hydroxycaprylic acid, hydroxycapric acid, glutaric acid, gluconic acid, or a combination of two or more thereof. In some embodiments, the alpha hydroxy acid(s) is selected from among mandelic acid, glycolic acid, citric acid, lactic acid, malic acid, tartaric acid, phytic acid, hydroxycaprylic acid, hydroxycapric acid and combinations thereof. In further embodiments, the alpha hydroxy acids are citric acid, mandelic acid, glycolic acid, lactic acid or a combination of two or more thereof. In at least one embodiment, the alpha hydroxy acid is lactic acid.

The amount of alpha hydroxyl acid(s) and/or a salt(s) thereof present in the personal care composition may range from about 0.1 to about 6 wt. %, based on the total weight of the personal care composition. For instance, the personal care compositions may include one or more alpha hydroxyl acid(s) and/or a salt(s) thereof in an amount from about 0.1 to about 5 wt. %, about 0.1 to about 4 wt. %, about 0.1 to about 3 wt. %, about 0.1 to about 2 wt. %; from about 0.5 to about 6 wt. %, about 0.5 to about 5 wt. %, about 0.5 to about 4 wt. %, about 0.5 to about 3 wt. %, about 0.5 to about 2 wt. %; from about 1 to about 6 wt. %, about 1 to about 5 wt. %, about 1 to about 4 wt. %, about 1 to about 3 wt. %, about 1 to about 2 wt. %; from about 2 to about 6 wt. %, about 2 to about 5 wt. %, about 2 to about 4 wt. %, about 2 to about 3 wt. %; from about 3 to about 6 wt. %, about 3 to about 5 wt. %, about 3 to about 4 wt. %, about 0.1 to about 3 wt. %; from about 4 to about 6 wt. %, about 4 to about 5 wt. %, or any range or subrange thereof, based on the total weight of the personal care composition.

The personal care compositions can comprise one or more beta hydroxy acid(s) or a salt thereof. Non-limiting examples of beta hydroxy acids include salicylic acid, propionic acid, beta-hydroxybutyric acid, beta-hydroxy beata-methylbutyric acid, carnitine, and combinations of two or more thereof. The beta hydroxy acids may in some cases be selected from salicylic acid, esters of salicylic acid, sodium salicylate, beta hydroxybutanoic acid, tropic acid, trethocanic acid, beta hydroxyl acids obtained from white willow bark extract and/or wintergreen leaves, and combinations of two or more thereof.

The amount of beta hydroxy acid(s) or salt(s) thereof in the personal care composition may be from about 0.05 to about 2 wt. %, about 0.05 to about 1.8 wt. %, about 0.05 to about 1.6 wt. %, about 0.05 to about 1.4 wt. %, about 0.05 to about 1.2 wt. %, about 0.05 to about 1 wt. %, about 0.05 to about 0.8 wt. %, about 0.05 to about 0.6 wt. %, about 0.05 to about 0.4 wt. %, about 0.05 to about 0.2 wt. %, about 0.05 to about 0.1 wt. %; from about 0.1 to about 2 wt. %, about 0.1 to about 1.8 wt. %, about 0.1 to about 1.6 wt. %, about 0.1 to about 1.4 wt. %, about 0.1 to about 1.2 wt. %, about 0.1 to about 1 wt. %, about 0.1 to about 0.8 wt. %, about 0.1 to about 0.6 wt. %, about 0.1 to about 0.4 wt. %; from about 0.3 to about 2 wt. %, about 0.3 to about 1.8 wt. %, about 0.3 to about 1.6 wt. %, about 0.3 to about 1.4 wt. %, about 0.3 to about 1.2 wt. %, about 0.3 to about 1 wt. %, about 0.3 to about 0.8 wt. %; from about 0.6 to about 2 wt. %, about 0.6 to about 1.8 wt. %, about 0.6 to about 1.6 wt. %, about 0.6 to about 1.4 wt. %, about 0.6 to about 1.2 wt. %, about 0.6 to about 1 wt. %; from about 0.9 to about 2 wt. %, about 0.9 to about 1.8 wt. %, about 0.9 to about 1.6 wt. %, about 0.9 to about 1.4 wt. %; from about 1.2 to about 2 wt. %, about 1.2 to about 1.8 wt. %, about 1.2 to about 1.6 wt. %; from about 1.5 to about 2 wt. %, about 1.5 to about 1.8 wt. %, or any range or subrange thereof, based on the total weight of the personal care composition.

The personal care composition can comprise one or more polyhydroxy acid(s) or a salt thereof. The polyhydroxy acids may include, but are not limited to, gluconolactone, gluconic acid, galactose, lactobionic acid, or combinations thereof. In some embodiments, the polyhydroxy acids are gluconolactone, lactobionic acid or combinations thereof. For instance, the polyhydroxy acid may be glucanodeltalactone. The amount of polyhydroxy acid(s) and/or a salt(s) thereof present in the personal care composition may range from about 0.1 to about 6 wt. %, based on the total weight of the personal care composition. For instance, the personal care compositions may include one or more polyhydroxy acid(s) and/or a salt(s) thereof in an amount from about 0.1 to about 5 wt. %, about 0.1 to about 4 wt. %, about 0.1 to about 3 wt. %, about 0.1 to about 2 wt. %; from about 0.5 to about 6 wt. %, about 0.5 to about 5 wt. %, about 0.5 to about 4 wt. %, about 0.5 to about 3 wt. %, about 0.5 to about 2 wt. %; from about 1 to about 6 wt. %, about 1 to about 5 wt. %, about 1 to about 4 wt. %, about 1 to about 3 wt. %, about 1 to about 2 wt. %; from about 2 to about 6 wt. %, about 2 to about 5 wt. %, about 2 to about 4 wt. %, about 2 to about 3 wt. %; from about 3 to about 6 wt. %, about 3 to about 5 wt. %, about 3 to about 4 wt. %, about 0.1 to about 3 wt. %; from about 4 to about 6 wt. %, about 4 to about 5 wt. %, or any range or subrange thereof, based on the total weight of the personal care composition.

The personal care composition may include one or more pH adjusters to increase or decrease the overall pH of the personal care composition. For example, one or more acids may be included to decrease the pH of the personal care composition. Examples of suitable acids for decreasing the pH of the personal care composition include, but are not limited to, citric acid, acetic acid, and the like. The personal care composition may include one or more bases, such as sodium hydroxide, potassium hydroxide and the like, to increase the pH of the personal care composition. Additional or alternative acids and bases that are suitable for adjusting the pH of the personal care composition are readily known to one of ordinary skill in the art.

The amount of the pH adjuster in the personal care composition may be based on the desired pH of the final personal care composition and/or product. For example, the total amount of the pH adjuster may range from about 0.05 to about 20 wt. %, based on the total weight of the personal care composition. In some instances, the total amount of pH adjuster is from about 0.05 to about 15 wt. %, about 0.1 to about 10 wt. %, or about 0.12 to about 5 wt. %, including ranges and sub-ranges therebetween, based on the total weight of the personal care composition.

In certain embodiments, the personal care composition has a pH of from about 3.5 to about 10.0. In other embodiments, the personal care composition has a pH of from about 3.5 to about 8.0. In some embodiments, the personal care composition has a pH of from about 3.5 to about 7.5. In other embodiments, the personal care composition has a pH of from about 3.5 to about 7.0. In further embodiments, the personal care composition has a pH of from about 3.5 to about 6.5. Still other embodiments provide personal care compositions having a pH of from about 3.5 to about 6.0. While other embodiments provide personal care compositions having a pH of from about 3.5 to about 5.5. Yet other embodiments provide personal care compositions having a pH of from about 3.5 to about 5.0. In certain embodiments, the personal care composition has a pH of from about 3.75 to about 4.5. In certain embodiments, the personal care composition is a body wash, having a pH of from about 4.0 to about 6.0. In other embodiments, the personal care composition is a body lotion, having a pH of from about 4.0 to about 5.0.

Additional ingredients may be present in the personal care composition. These include water and ingredients to thicken, preserve, emulsify, add fragrance, adjust the pH, and color. The personal care compositions may include any of the following additional ingredients in an amount of from about 0.01 to about 5 wt. %. In some instances, the amount of additional ingredients present in the personal care composition is from about 0.01 to about 4 wt. %, about 0.01 to about 3 wt. %, about 0.01 to about 2 wt. %, about 0.01 to about 1 wt. %, about 0.01 to about 0.5 wt. %, about 0.01 to about 0.1 wt. %; about 0.1 to about 5 wt. %, about 0.1 to about 4 wt. %, about 0.1 to about 3 wt. %, about 0.1 to about 2 wt. %, about 0.1 to about 1 wt. %, about 0.1 to about 0.5 wt. %, about 0.1 to about 0.1 wt. %; about 0.5 to about 5 wt. %, about 0.5 to about 4 wt. %, about 0.5 to about 3 wt. %, about 0.5 to about 2 wt. %, about 0.5 to about 1 wt. %; about 0.75 to about 5 wt. %, about 0.75 to about 4 wt. %, about 0.75 to about 3 wt. %, about 0.75 to about 2 wt. %, about 0.75 to about 1 wt. %; about 1 to about 5 wt. %, about 1 to about 4 wt. %, about 1 to about 3 wt. %, about 1 to about 2 wt. %; about 2 to about 5 wt. %, about 2 to about 4 wt. %, about 2 to about 3 wt. %; about 3 to about 5 wt. %, about 3 to about 4 wt. %, including any range or subrange therebetween, based on the total weight of the personal care composition.

The personal care composition can comprise additional ingredients, such as proteins (e.g., hydrolyzed vegetable protein, hydrolyzed wheat protein, hydrolyzed milk protein, hydrolyzed silk and hydrolyzed collagen), vitamins (e.g., panthenol, biotin, vitamin E acetate, vitamin A and D palmitate), moisturizers/humectants (e.g., glycerin, propylene glycol, sodium pyroglutamic acid (also known as PCA), amino acid-based surfactants, and HLA), emollients (e.g., esters, isopropyl myristate, decyl oleate, C12-15 alkyl benzoate), botanicals (e.g., chamomile, aloe, rosemary), as well as preservatives, dyes, pH adjusters and chelating agents. Additional examples of vitamins that may be included in some personal care compositions include tocopherol, retinol, and ascorbic acid. Vitamin derivatives, such as ascorbyl monopalmitate, tocopheryl acetate, and Vitamin E palmitate, may also be included in certain embodiments of the invention.

Non-limiting examples of fragrances and perfumes include odor compounds selected from: 7-acetyl-1,2,3,4,5,6,7,8-octahydro-1,1,6,7-tetramethylnaphthalene, α-ionone, β-ionone, γ-ionone α-isomethylionone, methylcedrylone, methyl dihydrojasmonate, methyl 1,6,10-trimethyl-2,5,9-cyclododecatrien-1-yl ketone, 7-acetyl-1,1,3,4,4,6-hexamethyltetralin, 4-acetyl-6-tert-butyl-1,1-dimethylindane, hydroxyphenylbutanone, benzophenone, methyl β-naphthyl ketone, 6-acetyl-1,1,2,3,3,5-hexamethylindane, 5-acetyl-3-isopropyl-1,1,2,6-tetramethylindane, 1-dodecanal, 4-(4-hydroxy-4-methylpentyl)-3-cyclohexene-1-carboxaldehyde, 7-hydroxy-3,7-dimethyloctanal, 10-undecen-1-al, isohexenylcyclohexylcarboxaldehyde, formyltricyclodecane, condensation products of hydroxycitronellal and methyl anthranilate, condensation products of hydroxycitronellal and indole, condensation products of phenylacetaldehyde and indole, 2-methyl-3-(para-tert-butylphenyl)propionaldehyde, ethylvanillin, heliotropin, hexylcinnamaldehyde, amylcinnamaldehyde, 2-methyl-2-(isopropylphenyl)propionaldehyde, coumarin, γ-decalactone, cyclopentadecanolide, 16-hydroxy-9-hexadecenoic acid lactone, 1,3,4,6,7,8-hexahydro-4,6,6,7,8,8-hexamethylcyclopenta-γ-2-benzopyran, β-naphthol methyl ether, ambroxane, dodecahydro-3a,6,6,9a-tetramethylnaphtho[2,1b]furan, cedrol, 5-(2,2,3-trimethylcyclopent-3-enyl)-3-methylpentan-2-ol, 2-ethyl-4-(2,2,3-trimethyl-3-cyclopenten-1-yl)-2-buten-1-ol, caryophyllene alcohol, tricyclodecenyl propionate, tricyclodecenyl acetate, benzyl salicylate, cedryl acetate, and tert-butylcyclohexyl acetate.

Other fragrances may include odor compounds selected from essential oils, resinoids and resins from a large number of sources, such as, for example, Peru balsam, olibanum resinoid, *styrax*, labdanum resin, nutmeg, *cassia* oil, benzoin resin, coriander, and lavandin.

Further suitable fragrances include odor compounds selected from phenylethyl alcohol, terpineol, linalool, linalyl acetate, geraniol, nerol, 2-(1,1-dimethylethyl)cyclo-hexanol acetate, benzyl acetate, and eugenol. The fragrances or perfumes can be used as single substances or in a mixture with one another.

The personal care composition may further comprise one or more colorants. The colorants may be a pigment, a dye, or mixtures thereof. Non-limiting examples of pigments include titanium dioxide, Zinc Oxide, Kaolin, Mica etc. Non-limiting examples of dyes include food dyes suitable for food, drug and cosmetic applications, and mixtures thereof. Some color agents (colorants) are known as FD&C dyes.

The colorants may be present in an amount ranging from about 0.0001% wt. % to about 0.4% wt. %, including all percentages and subranges therebetween, based on the total weight of the personal care composition. In some embodiments, the colorants may be present in an amount ranging from about 0.0001% wt. % to about 4% wt. %, including all percentages and subranges therebetween, based on the total weight of the personal care composition.

In certain embodiments, in order to prevent ingredients from separating, emulsifiers may be added. In certain embodiments, additional ingredients may include conditioning agents that moisturize the skin during and after use of the personal care composition.

In other embodiments, the composition may include any of following materials in any desired amount to achieve a desired effect in the composition (amounts that can be used in some embodiments are provided): one or more alkaline salts, for example, sodium chloride, sodium sulfate, sodium carbonate, sodium bicarbonate and/or their equivalents (0 to 5 wt. %); sequestrants, for example, tetrasodium EDTA, and/or their equivalents (0 to 2 wt. %); biocides, for example, Triclosan (2,4,4'-trichloro-2'-hydroxydiphenyl ether), DMDM hydantoin, formaldehyde and/or imidazolidinyl urea, and/or their equivalents (0 to 2 wt. %); organic acids, for example, citric acid and/or formic acid and/or their equivalents (0 to 2 wt. %); viscosity modifiers (0 to 2 wt. %); fragrances and/or perfumes (0 to 5 wt. %); preservatives, for example, phenoxyethanol, formaldehyde solution, parabens, pentanediol or sorbic acid (0 to 2 wt. %); pearlizing agents, for example, glycol distearic esters, such as ethylene glycol distearate, but also fatty acid monoglycol esters (0 to 3 wt. %); stabilizers, for example, metal salts of fatty acids, such as e.g. magnesium stearate, aluminum stearate and/or zinc stearate (0 to 2 wt. %); and dyes and pigments that are approved and suitable for cosmetic purposes.

The personal care compositions may be aqueous and, e.g., include water in an amount from about 1 to about 95 wt. %, based on the total weight of the personal care composition. For example, the water may be present in the personal care composition in an amount from about 5 to about 95 wt. %, about 10 to about 95 wt. %, about 15 to about 95 wt. %, about 20 to about 95 wt. %, about 30 to about 95 wt. %, about 40 to about 95 wt. %, about 50 to about 95 wt. %, about 60 to about 95 wt. %, about 70 to about 95 wt. %, about 80 to about 95 wt. %, about 90 to about 95 wt. %; about 5 to about 90 wt. %, about 10 to about 90 wt. %, about 15 to about 90 wt. %, about 20 to about 90 wt. %, about 30 to about 90 wt. %, about 40 to about 90 wt. %, about 50 to about 90 wt. %, about 60 to about 90 wt. %, about 70 to about 90 wt. %, about 80 to about 90 wt. %; about 5 to about 80 wt. %, about 10 to about 80 wt. %, about 15 to about 80 wt. %, about 20 to about 80 wt. %, about 30 to about 80 wt. %, about 40 to about 80 wt. %, about 50 to about 80 wt. %, about 60 to about 80 wt. %, about 70 to about 80 wt. %; about 5 to about 70 wt. %, about 10 to about 70 wt. %, about 15 to about 70 wt. %, about 20 to about 70 wt. %, about 30 to about 70 wt. %, about 40 to about 70 wt. %, about 50 to about 70 wt. %, about 60 to about 70 wt. %; about 5 to about 60 wt. %, about 10 to about 60 wt. %, about 15 to about 60 wt. %, about 20 to about 60 wt. %, about 30 to about 60 wt. %, about 40 to about 60 wt. %, about 50 to about 60 wt. %; about 5 to about 50 wt. %, about 10 to about 50 wt. %, about 15 to about 50 wt. %, about 20 to about 50 wt. %, about 30 to about 50 wt. %, about 40 to about 50 wt. %, including any ranges and subranges therebetween, based on the total weight of the personal care composition.

In some embodiments, the personal care compositions are substantially free of water or are free of water. For instance, the personal care compositions may include about 5 wt. % or less, about 4 wt. % or less, about 3 wt. % or less, about 2 wt. % or less, about 1 wt. % or less, or about 0.5 wt. % or less of water, based on the total weight of the personal care compositions. In one embodiment, the personal care composition has about 0 wt. % of water, based on the total weight of the personal care compositions.

Aspects of the invention are directed to methods for improving skin by applying one or more personal care compositions. In some embodiments, the methods include applying one or more (e.g., two, three, four, five, six, or seven personal care compositions). The methods may employ the personal care compositions disclosed herein.

The methods and personal care compositions disclosed herein may be used to alleviate, mitigate, and/or treat skin suffering from dryness, hypersensitivity, atopic dermatitis, acne, psoriasis, and the like.

According to one embodiment, provided is a method for improving skin that includes:
(I) applying a cleaning composition to a section of skin, the cleaning composition comprising:
   (a) from about 1 to about 25 wt. % of a surfactant,
   (b) from about 0.1 to about 5 wt. % of a polysaccharide,
   (c) from about 0.01 to about 5 wt. % of a fatty alcohol, and
   (d) from about 0.5 to about 7 wt. % of a post-biotic blend, wherein all weight percentages are based on the total weight of the cleaning composition; and
(II) rinsing the section of skin;
(II) applying a lotion composition to the section of skin, the lotion comprising:
   (a) from about 1 to about 30 wt. % of a silicone, an oil, a polyol, an emollient or a combination thereof,
   (b) from about 0.1 to about 5 wt. % of a polysaccharide,
   (c) from about 0.01 to about 5 wt. % of a fatty alcohol, and
   (d) from about 0.5 to about 7 wt. % of a post-biotic blend,
      wherein all weight percentages are based on the total weight of the lotion composition.

The methods typically include applying an effective amount of the cleaning composition to a section of skin. The amount of the cleaning composition applied to the skin may be about 0.1 to about 5 grams/inch$^2$ of skin. In some cases, the amount of cleaning composition applied to the skin is about 0.1 to about 3 grams/inch$^2$, about 0.1 to about 2 grams/inch$^2$, about 0.1 to about 1 grams/inch$^2$; about 0.5 to about 3 grams/inch$^2$, about 0.5 to about 2 grams/inch$^2$, about 0.5 to about 1 grams/inch$^2$; about 1 to about 3 grams/inch$^2$, about 1 to about 2 grams/inch$^2$; about 1.5 to about 3 grams/inch$^2$, about 1.5 to about 2 grams/inch$^2$, including any ranges or subranges therebetween. The composition is spread on the skin neat, or it may be mixed with water. The spreading of the cleaning composition may be done by hand, or it may be done by an instrument such as a glove or a piece of cloth.

Usually, the cleaning composition is allowed to remain on the skin for a period of time sufficient to clean the section of skin—for example, for about 1 second to about 1 minute, about 1 to about 45 seconds, about 1 to about 30 seconds, or about 1 to about 15 seconds. As is common, the skin may be wetted or rinsed with water prior to the application of the cleaning composition. Having the skin wetted before applying the cleaning composition may be beneficial for enhancing the effects of certain cleaning compositions according to aspects of the invention.

The method may, in some cases, include a step of drying the section of skin before applying the lotion composition to the section of skin. The skin may be dried by towel, hair drier, or other means, e.g., depending on the desired degree of dryness before the application of the lotion composition.

The methods typically include applying an effective amount of the lotion composition to a section of skin. The amount of the lotion composition applied to the skin may be about 0.1 to about 5 grams/inch$^2$ of skin. In some cases, the amount of lotion composition applied to the skin is about 0.1 to about 3 grams/inch$^2$, about 0.1 to about 2 grams/inch$^2$, about 0.1 to about 1 grams/inch$^2$; about 0.5 to about 3 grams/inch$^2$, about 0.5 to about 2 grams/inch$^2$, about 0.5 to about 1 grams/inch$^2$; about 1 to about 3 grams/inch$^2$, about 1 to about 2 grams/inch$^2$; about 1.5 to about 3 grams/inch$^2$, about 1.5 to about 2 grams/inch$^2$, including any ranges or subranges therebetween. As mentioned above with regarding to the cleaning composition, the lotion composition may be spread by hand, or it may be done by an instrument, such as a glove or a piece of cloth.

EXAMPLES

Example 1

Two exemplary, non-limiting, personal care compositions of the present invention (Ex. A and Ex. B) are prepared in accordance with the formulations shown in Table 1 & 2 (below). The compositions are in the form of an oil in water lotion and a body wash.

TABLE 1

| Ingredient | Ex. A Wt. % | Comp. Ex. 1 Wt. % |
|---|---|---|
| Inulin | 0-1 | — |
| Butyloctanol | 0.4-2 | — |
| Stearyl Alcohol | 1-8 | 1-8 |
| Cetyl Alcohol | 1-10 | 1-10 |
| Sodium Pyruvate | 0.02-0.22 | — |
| Lactic Acid | 0.2-0.8 | — |
| Dipalmitoylethyl Dimonium Chloride (and) Cetearyl Alcohol (and) Glycerin | 0-2 | 0-2 |
| Cetearyl Alcohol and Ceteareth-20 | 1-5 | 1-5 |
| Isopropyl Palmitate | 0-4 | 0-4 |
| Coco-Caprylate | 0-3 | 0-3 |
| Diethylhexyl Carbonate | 0-3 | 0-3 |

TABLE 1-continued

| Ingredient | Ex. A | Comp. Ex. 1 Wt. % |
|---|---|---|
| Glycerin | 2-10 | 2-10 |
| Caprylyl Glycol | 0-2 | 0-2 |
| Cocoglycerides | 0-5 | 0-5 |
| Sodium Benzoate | 0.2-1 | 0.2-1 |
| Citric Acid | — | 0-1 |
| Water | 75-80 | Q.S. to 100 |

TABLE 2

| Ingredient | Ex.B | Comp. Ex. 2 Wt. % |
|---|---|---|
| Inulin | 0.5-5 | — |
| Butyloctanol | 0.02-0.2 | — |
| Sodium Pyruvate | 0.1-0.3 | — |
| Lactic Acid | 0.1-1 | — |
| Citric acid | — | 0.1-1 |
| Glycerin | 0-10 | 0-10 |
| Sodium C14-C16 Olefin Sulfonate | 3-5 | 3-5 |
| Cocamidopropyl Betaine | 4-6 | 4-6 |
| Poloxamer 124 | 0-0.1 | 0-0.1 |
| Sodium Benzoate | 0.4-0.6 | 0.4-0.6 |
| Hydroxyacetophenone | 0.1-0.5 | 0.1-0.5 |
| Sodium Gluconate | 0.05-0.5 | 0.05-0.5 |
| Sodium L-2-pyrrolidone-5-carboxylate | 0.1-1 | 0.1-1 |
| Polyquaternium-7 | 0.05-0.2 | 0.05-0.2 |
| Zinc Sulfate | 0.1-1 | 0.1-1 |
| Water | 75-80 | Q.S. to 100 |

TABLE 3

| Comp. Ex. 3 | Comp. Ex. 4 |
|---|---|
| Aqua/Water, | water (aqua), |
| Butyrospermum Parkii Butter/Shea Butter, | cocamidopropyl betaine, |
| Glycerin, | sodium hydroxypropyl starch phosphate, |
| Dimethicone, | |
| Niacinamide, | lauric acid, |
| Paraffinum Liquidum/Mineral Oil. | sodium lauroyl glycinate, |
| Cetearyl Alcohol, | sodium lauroyl isethionate, |
| Brassica Campestris Oleifera Oil/Rapeseed Seed Oil, | hydrogenated soybean oil, Glycine soja (soybean) oil, |
| Ammonium Polyacryldimethyltauramide/Ammonium Polyacryloyldimethyl Taurate, | sodium chloride, glycerin, fragrance (parfum), |
| Peg-100 Stearate, | phenoxyethanol, |
| Glyceryl Stearate, | guar hydroxypropyltrimonium chloride, |
| Peg-20 Methyl Glucose Sesquistearate, | |
| Cera Microcristallina/Microcrystalline Wax. Paraffin, | stearic acid, citric acid, |
| Sorbitan, | Sodium Isethionate, |
| Tristearate, | BHT, |
| Dimethiconol, | tetrasodium EDTA, |
| Mannose, | iodopropynyl butylcarbamate. |
| Disodium EDTA, | |
| Capryloyl Glycine, | |
| Vitreoscilla Ferment, | |
| Xanthan Gum, | |
| Pentaerythrityl Tetra-Di-T-Butyl, | |
| Hydroxyhydrocinnamate, | |
| Sodium Benzoate. | |

Example 2

In vitro experimentation was performed to assess the effect of Ex. A on bacteria residing on the skin in comparison to two comparative compositions (Comp. Ex. 1 and Comp. Ex. 3). Comp. Ex. 1 is a benchmark composition having a similar formula to Ex. A, except that Comp. Ex. 1 does not include the inventive combination of: a polysaccharide, a fatty alcohol, and a post-biotic blend, of Ex. A. Comp. Ex. 3 is a commercially available lotion. The list of ingredients for Comp. Ex. 3 is shown above in Table 3.

Specifically, human skin samples having about 8×3 mm (Ø×thickness) were used for the in vitro experimentation. 6 skin samples were used to assess skin penetration and 6 skin samples were used to evaluate skin biomarkers. The skin was obtained during abdominal plastic surgery from informed volunteers. The skin samples were cultured up to the planned endpoints.

A 4 µl sample of Ex. A, Comp. Ex. 1 or Comp. Ex. 3 is applied to respective skin samples once a day for 6 days. The samples of Ex. A are spread to cover the skin samples with a 6 Ø mm delivery membrane. Before each application of a sample, the skin samples were gently cleaned with a cogon pad.

To evaluate skin penetration, the 6 skin samples are stained with Rhodamine B, cryo-fixed and cut at the cryostat for consequent image acquisition and analysis. The analysis of Rhodamine B fluorescence is performed within the epidermis area. Fluorescent images are acquired and analyzed for two sections of each skin sample (6 skin samples×2 sections=12 sampling points/data for the tested condition). For each fluorescent image, the epidermis is analyzed by evaluating the fluorescence through Image-J application (NIH, USA). The obtained value is then normalized upon the dimension of the selected area.

To evaluate skin barrier biomarkers, the skin samples are immunostained with the selected antibody (SantaCruz cat #sc-66192) for Filaggrin, Involucrin, Desmocollin 1 and Claudin 1. The amount of the antigen present is evaluated at two sections for each skin sample (6 skin samples×2 sections=12 sampling points/data for the tested condition) by estimating the intensity and the distribution of the pink/red within the epidermis using Image J (NIH-USA). The obtained data is normalized upon the dimension of the analyzed surface expressed in pixels.

All quantitative data are summarized in terms of the mean score for each treatment. The measures of variation, as standard deviation, are applied to the original scores. Differences between groups are evaluated by one-way Anova with permutation test followed by Tukey's test with permutation.

Figure 1B:
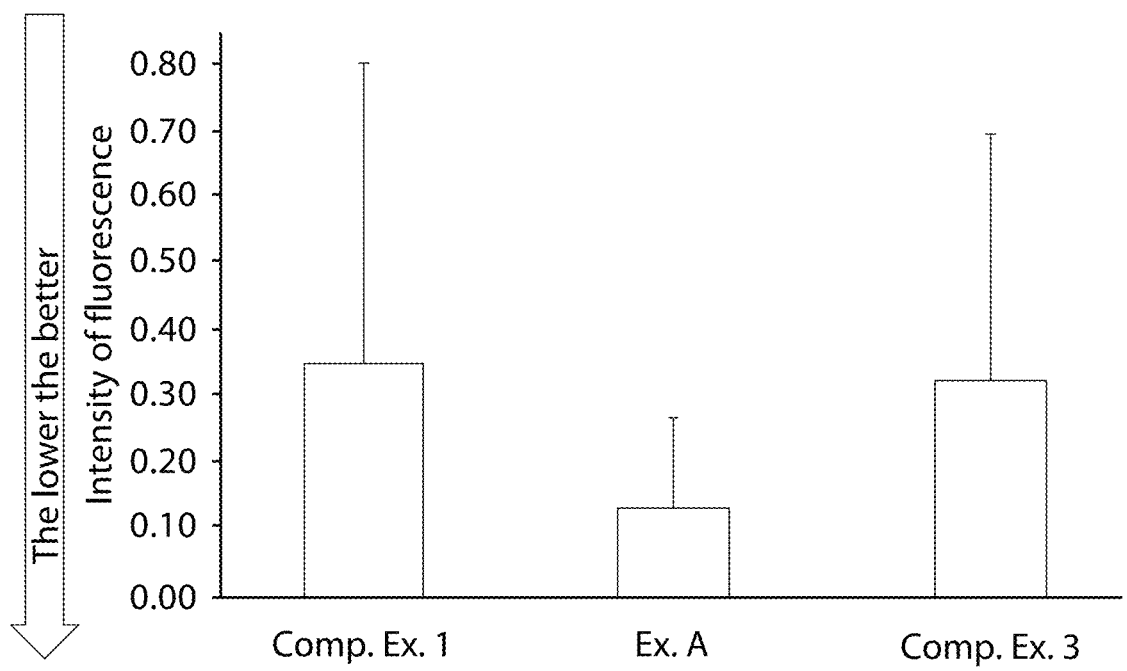
FIG. 1B is a bar graph of the amount of dye that penetrated into the skin samples after receiving an application of an exemplary personal care composition or comparative personal care compositions in accordance with an aspect of the invention.
Figure 2A:
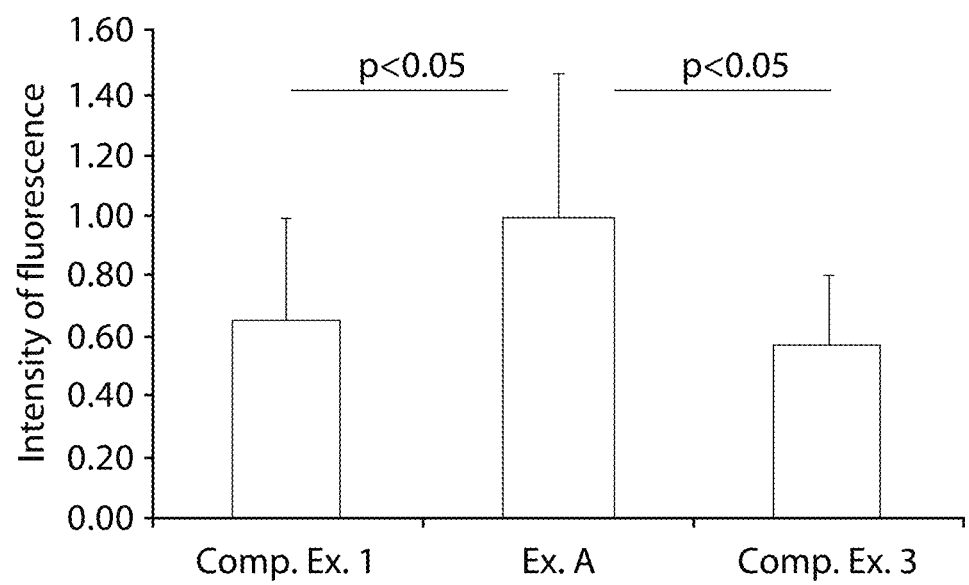
FIG. 2A is a bar graph depicting the effect of an exemplary personal care composition and comparative personal care compositions on filaggrin biomarkers for skin samples in accordance with an aspect of the invention.
Figure 2B:
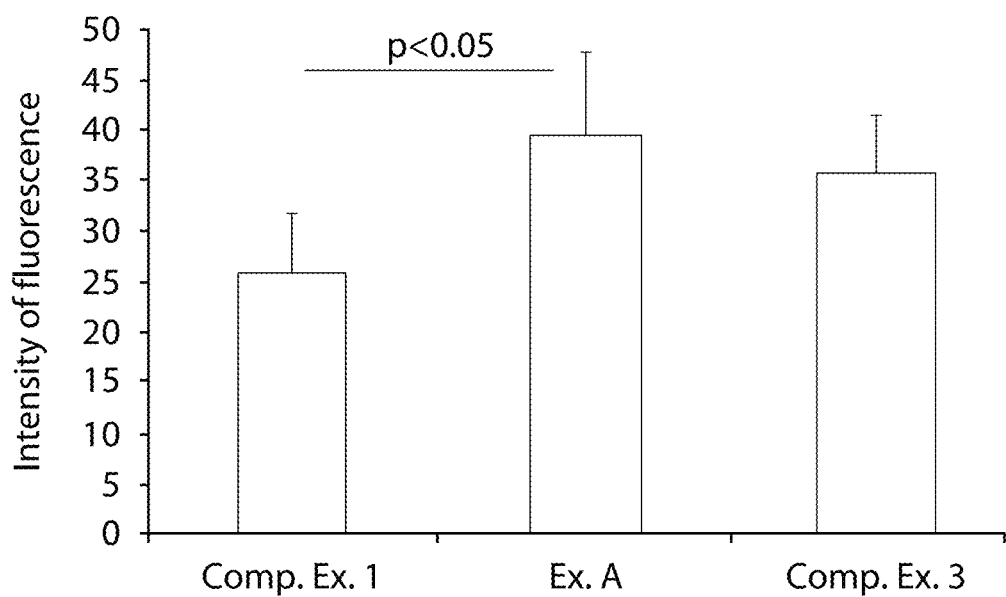
FIG. 2B is a bar graph depicting the effect of an exemplary personal care composition and comparative personal care compositions on involucrin biomarkers for skin samples in accordance with aspects of the invention.
Figure 2C:
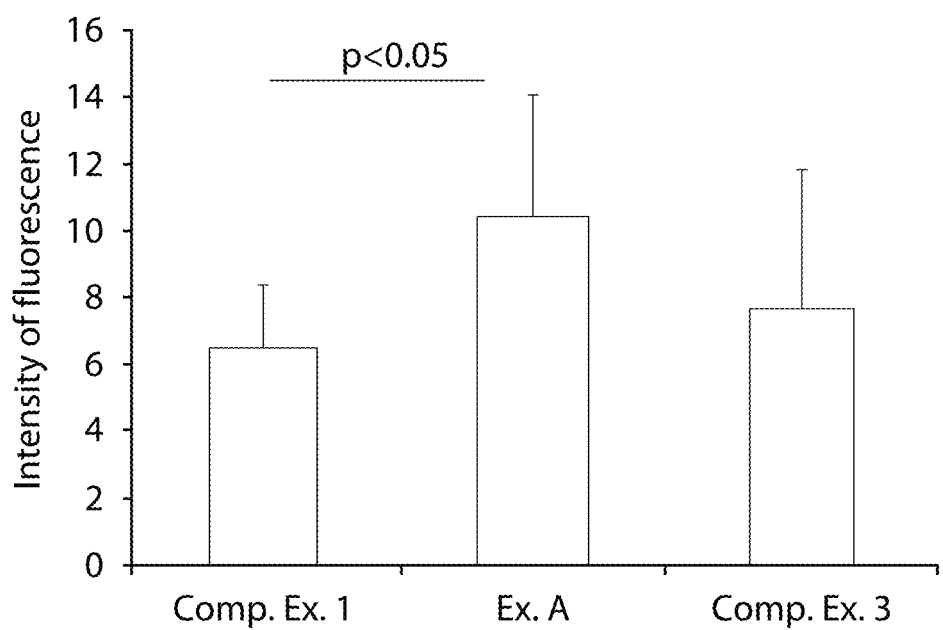
FIG. 2C is a bar graph depicting the effect of an exemplary personal care composition and comparative personal care compositions on desmocollin 1 biomarkers for skin samples in accordance with an aspect of the invention.
Figure 2D:
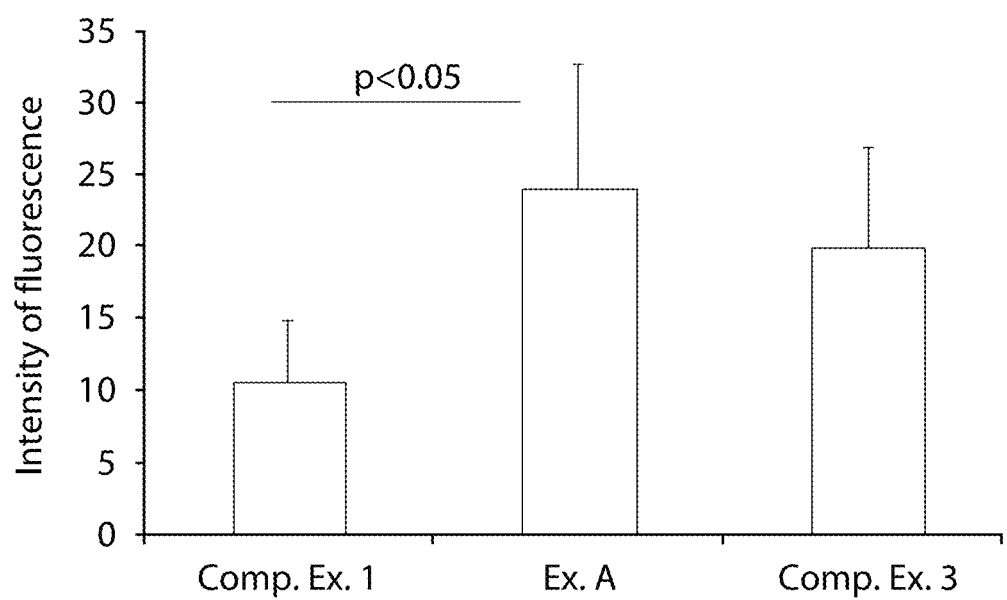
FIG. 2D is a bar graph depicting the effect of an exemplary personal care composition and comparative personal care compositions on claudin 1 biomarkers for skin samples in accordance with aspects of the invention.

The results establish that Ex. A enhances and strengthens skin barrier integrity. As shown in FIGS. 1A and 1B, the skin samples that received Ex. A exhibit less dye penetration as compared to Comp. Ex. 1 and Comp. Ex. 3. The less dye penetration, the stronger the skin barrier provided by the respective composition. In addition, Ex. A boosts skin barrier biomarkers, e.g., Filaggrin, Involucrin, Desmocollin 1 and Claudin 1, as compared to Comp. Ex. 1 and Comp. Ex. 3. (see, e.g., FIGS. 2A-2D).

Example 3

A growth inhibition assay was conducted to evaluate the effect of Example Composition A on the inhibition or growth of bacteria found on skin. Pure colonies of *E. coli, C. striatum, S. aureus* and *S. epidermidis* were grown in TSB medium overnight. The turbidity of the bacterial culture solution was adjusted to OD=0.1 (Optical Density) at 610 nm using a UV-VIS Spectrometer. Two 2 ml of the bacteria culture solution was incubated with a 2 ml sample of Ex. A, Comp. Ex. 1 or Comp. Ex. 3 for 48 hours.

Figure 3A:
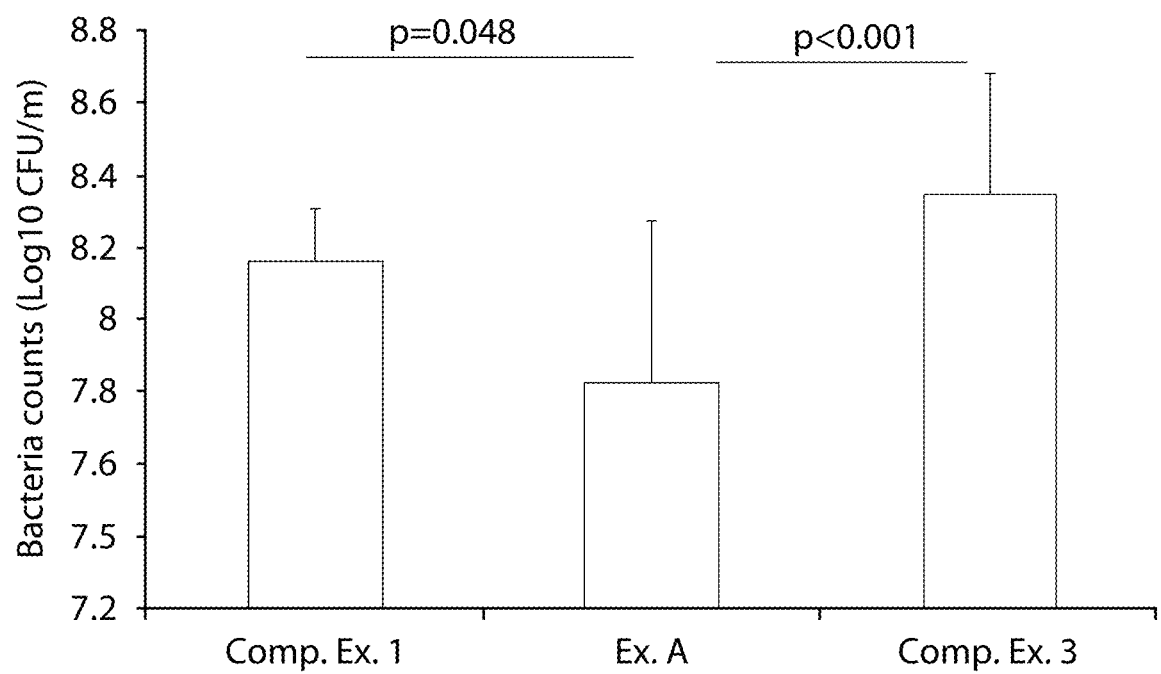
FIGS. 3A and 3B are bar graphs showing the growth of S. aureus and S. epidermidis, respectively, after application of another exemplary personal care composition and comparative personal care compositions in accordance with an aspect of the invention.
Figure 3B:
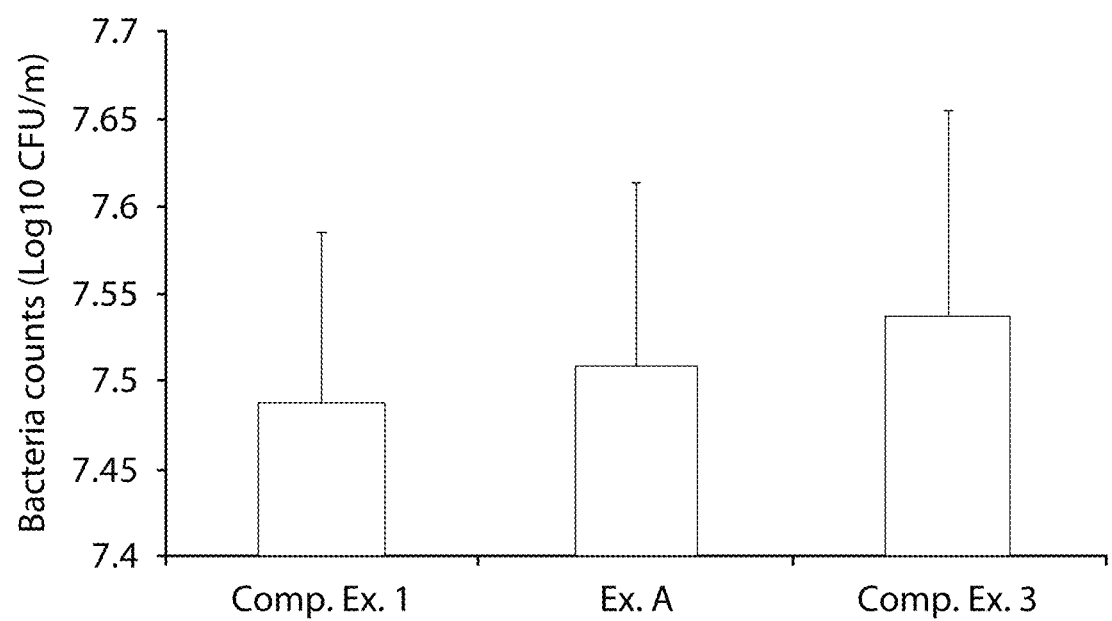

The turbidity of each tube was read after incubation. Replicates were run for each treatment. FIGS. 3A and 3B are bar graphs depicting the growth of *S. aureus* and *S. epidermidis* after application of Ex. A, Comp. Ex. 1 and Comp. Ex. 3.

Figure 3C:
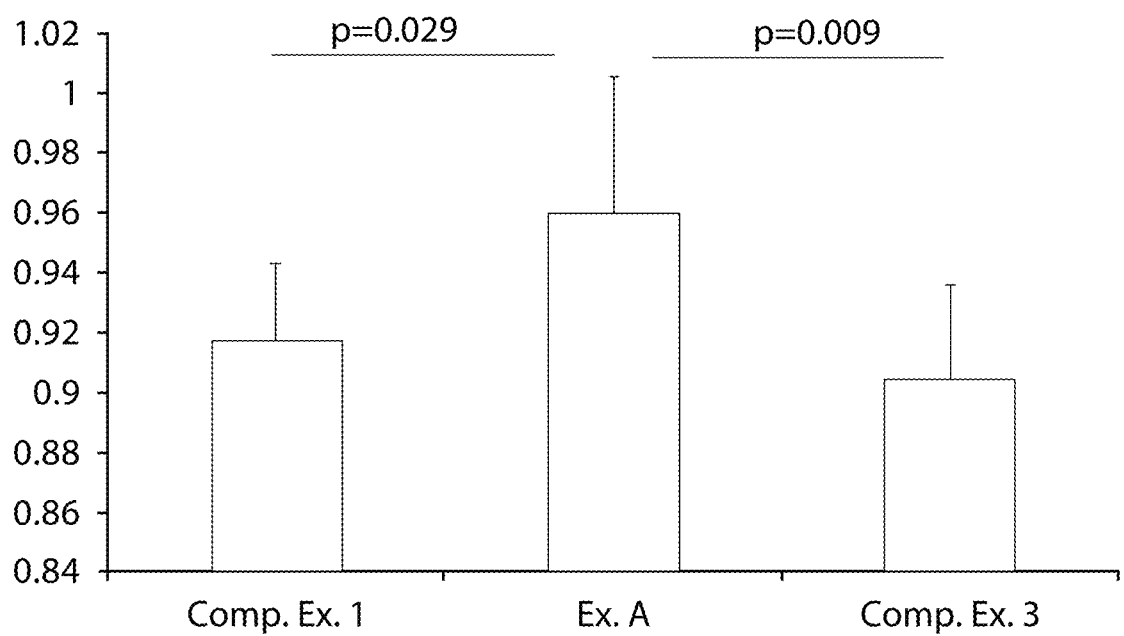
FIG. 3C is a bar graph depicting the ratio of desirable bacteria to undesirable bacteria after application of an exemplary personal care composition and comparative personal care compositions in accordance with an aspect of the invention.

FIG. 3C is a bar graph showing the ratio of desirable bacteria to undesirable bacteria after application of Ex. A, Comp. Ex. 1, and Comp. Ex. 3. As shown in FIG. 3C, Ex. A inhibited the growth of *S. aureus*, but promoted *S. epidermidis*.

Example 4

An exemplary, non-limiting personal care composition (Ex. B) was prepared in accordance with the formulation shown in Table 2 (above). Ex. B is in the form of a body wash.

Example 5

The effect of Ex. B on the growth of various bacteria residing on the skin was evaluated in comparison to two comparative compositions (Comp. Ex. 2 and Comp. Ex. 4). Comp. Ex. 2 was a benchmark composition having a similar formula to Ex. B, except that Comp. Ex. 2 does not include the invention combination of a polysaccharide, a fatty alcohol, and a post-biotic blend that is contained in Ex. B. Comp. Ex. 4 was a commercially available body wash. The list of ingredients for Comp. Ex. 4 is shown above in Table 3.

Specifically, growth inhibition assays were conducted to evaluate the effect of Example Composition B has on the inhibition or growth of bacteria found on skin. Pure colonies of *E. coli*, *C. striatum*, and *S. epidermidis* were grown in TSB medium overnight. The turbidity of the bacterial culture solution was adjusted to OD=0.1 (Optical Density) at 610 nm using a UV-VIS Spectrometer. Two 2 ml of the bacteria culture solution was incubated with a 2 ml sample of Ex. B, Comp. Ex. 2 or Comp. Ex. 4 for 48 hours.

Figure 4A:
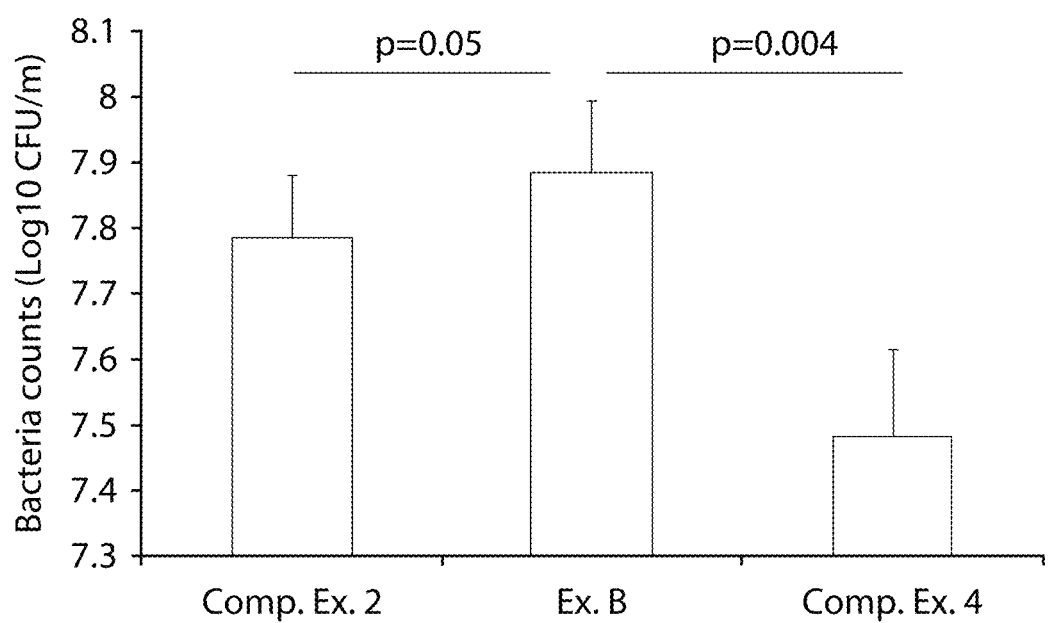
FIG. 4A is a bar graph depicting the growth of S. epidermidis, after application of an exemplary personal care composition and comparative personal care compositions in accordance with aspects of the invention.
Figure 4B:
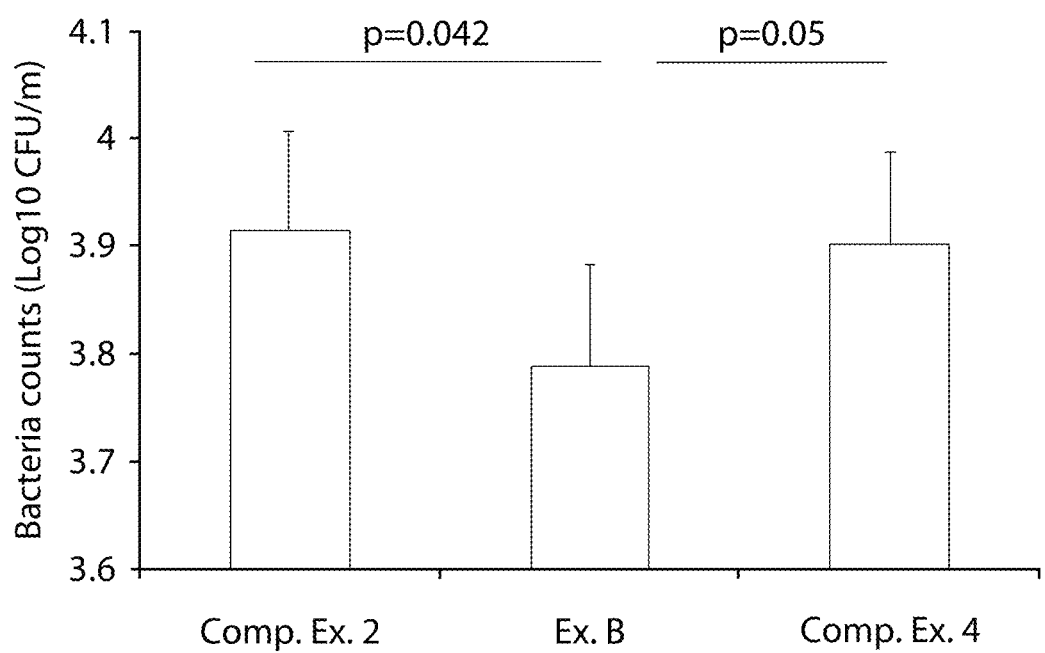
FIG. 4B is a bar graph showing the growth of C. striatum after application of an exemplary personal care composition and comparative personal care compositions in accordance with an aspect of the invention.
Figure 4C:
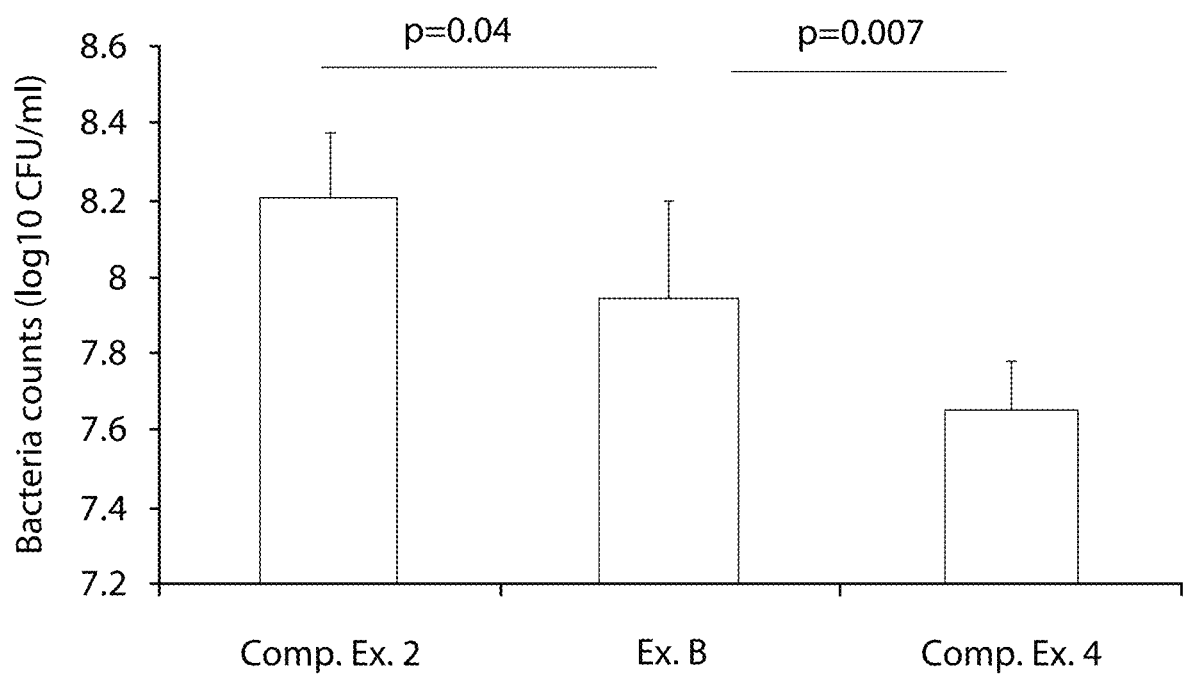
FIG. 4C is a bar graph showing the growth of E. coli after application of an exemplary personal care composition and comparative personal care compositions in accordance with aspects of the invention.
Figure 5A:
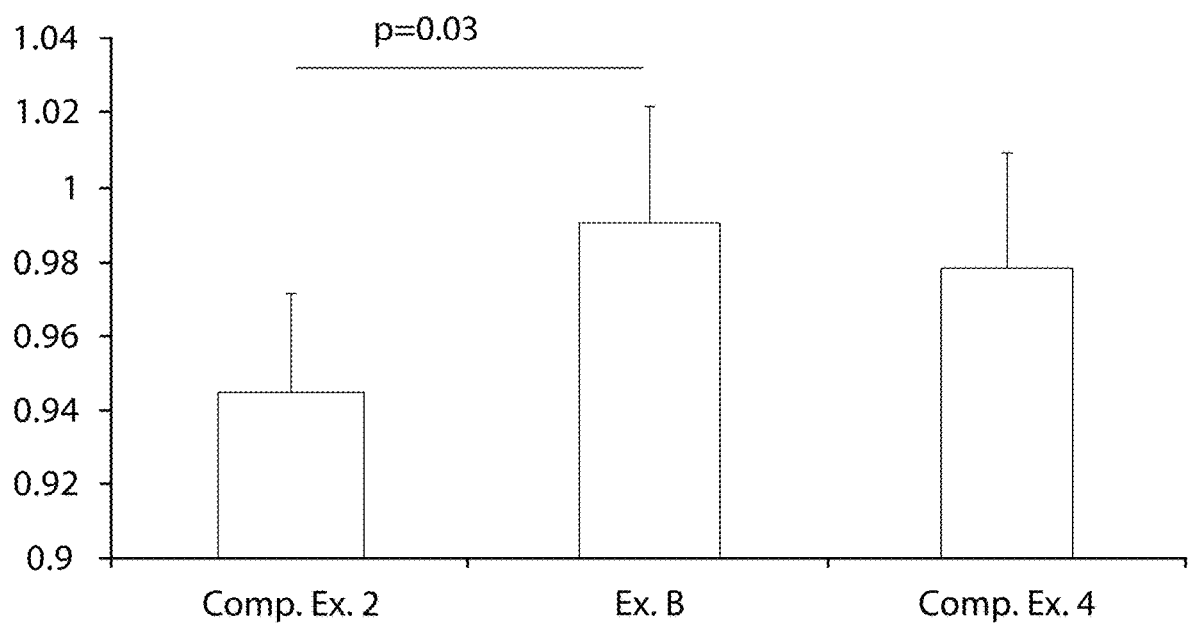
FIG. 5A is a bar graph showing the ratio of S. epidermidis to E. coli after application of an exemplary personal care composition and comparative personal care compositions in accordance with an aspect of the invention.
Figure 5B:
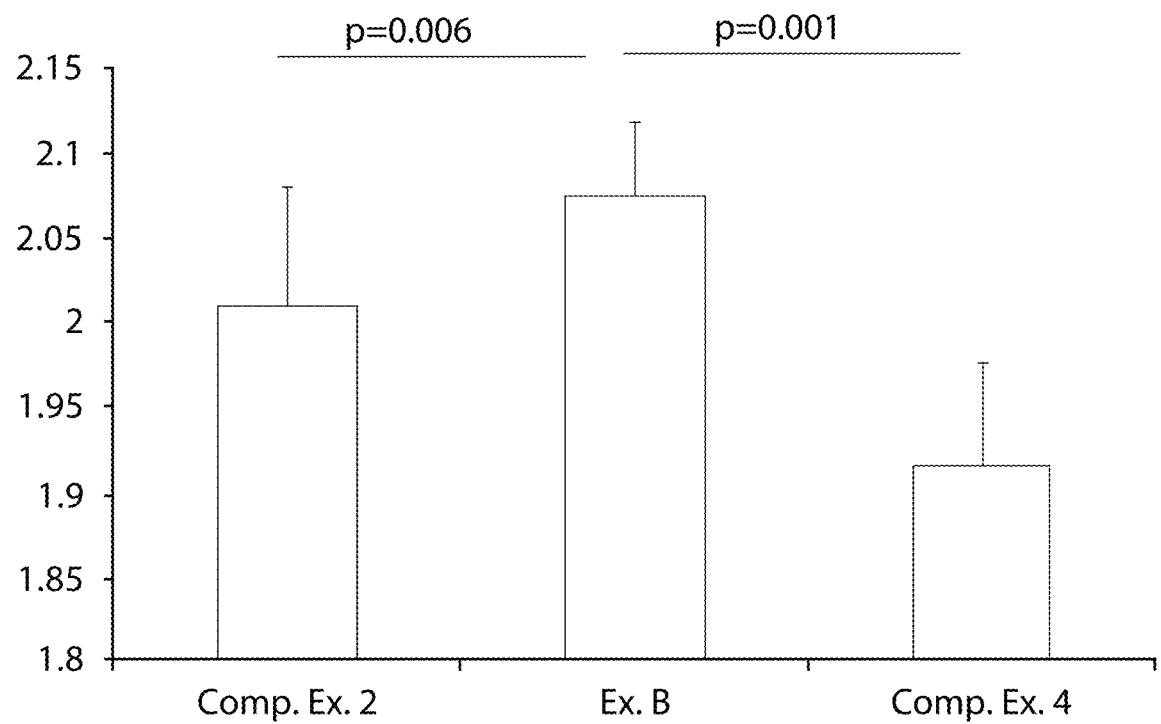
FIG. 5B is a bar graph showing the ratio of S. epidermidis to C. striatum after application of another exemplary personal care composition and comparative personal care compositions in accordance with aspects of the invention.

The turbidity of each tube was read after incubation. Replicates were run for each treatment. FIGS. 4A-4C are bar graphs showing the growth of *S. epidermidis*, *C. striatum*, and *E. coli* after application of Ex. B, Comp. Ex. 2 and Comp. Ex. 4. FIG. 5A is a bar graph showing the ratio of *S. epidermidis* to *E. coli* after application of Ex. B, Comp. Ex. 2 and Comp. Ex. 4. FIG. 5B is a bar graph showing the ratio of *S. epidermidis* to *C. striatum* after application of Ex. B, Comp. Ex. 2 and Comp. Ex. 4.

Example 6

An exemplary, non-limiting personal care composition (Ex. D) was prepared in accordance with aspects of the invention. Example Composition D was in the form of a lotion and contained 0.6 wt. % of lactic acid, 0.15 wt. % of sodium pyruvate, 1 wt. % of inulin, and 0.05 wt. % of butyloctanol, with all weight percentages being based on the total weight of the personal care composition. A comparative composition (Comp. Ex. 5) was prepared having a similar formula to as Ex. D, except that Comp. Ex. 5 did not include the polysaccharide, fatty alcohols, or post-biotic blend of Ex. D.

Example 7

The effect of Ex. D on the growth of various bacteria residing on skin was evaluated in comparison to two comparative compositions (Comp. Exs. 5 and 6). Comp. Ex. 6 was a commercially available body wash.

Specifically, growth inhibition assays were conducted to evaluate the effect of Ex. D on the inhibition or growth of bacteria found on skin. Pure colonies of *S. aureus* and *S. epidermidis* were grown in TSB medium overnight. The turbidity of the bacterial culture solution was adjusted to OD=0.1 (Optical Density) at 610 nm using a UV-VIS Spectrometer. Two 2 ml of the bacteria culture solution was incubated with a 2 ml sample of Ex. D, Comp. Ex. 5, or Comp. Ex. 6 for 48 hours.

Figure 6A:
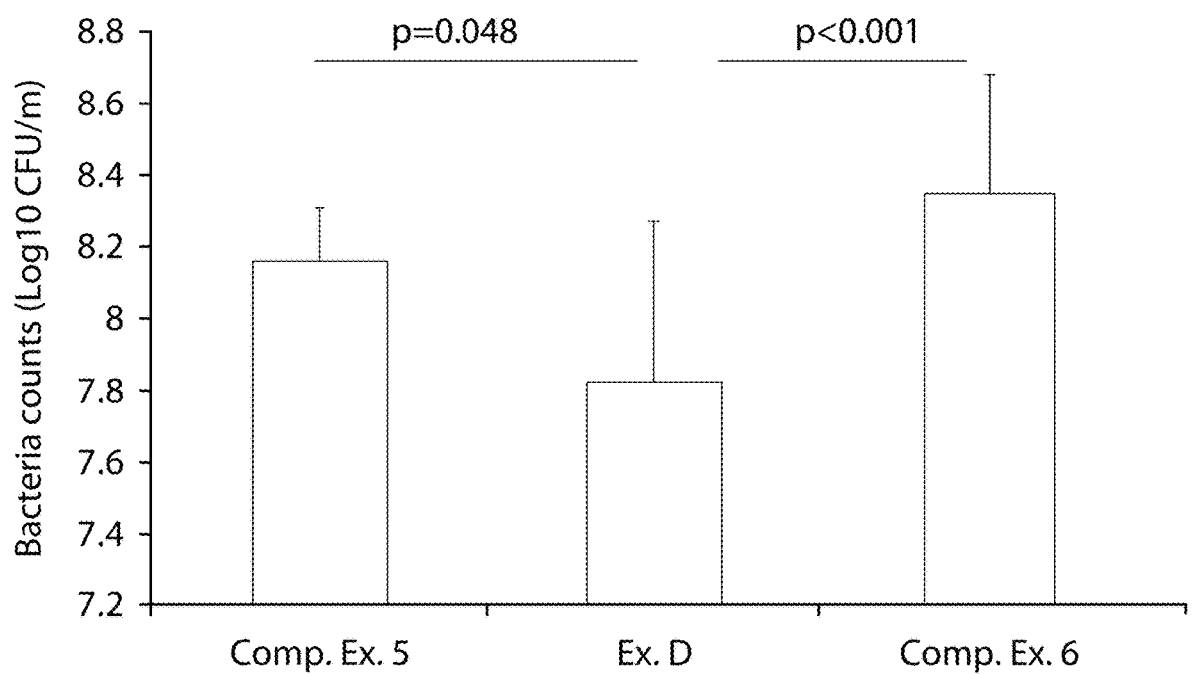
FIGS. 6A and 6B are bar graphs showing the growth of S. aureus and S. epidermidis, respectively, after application of another exemplary personal care composition and comparative personal care compositions in accordance with an aspect of the invention.
Figure 6B:
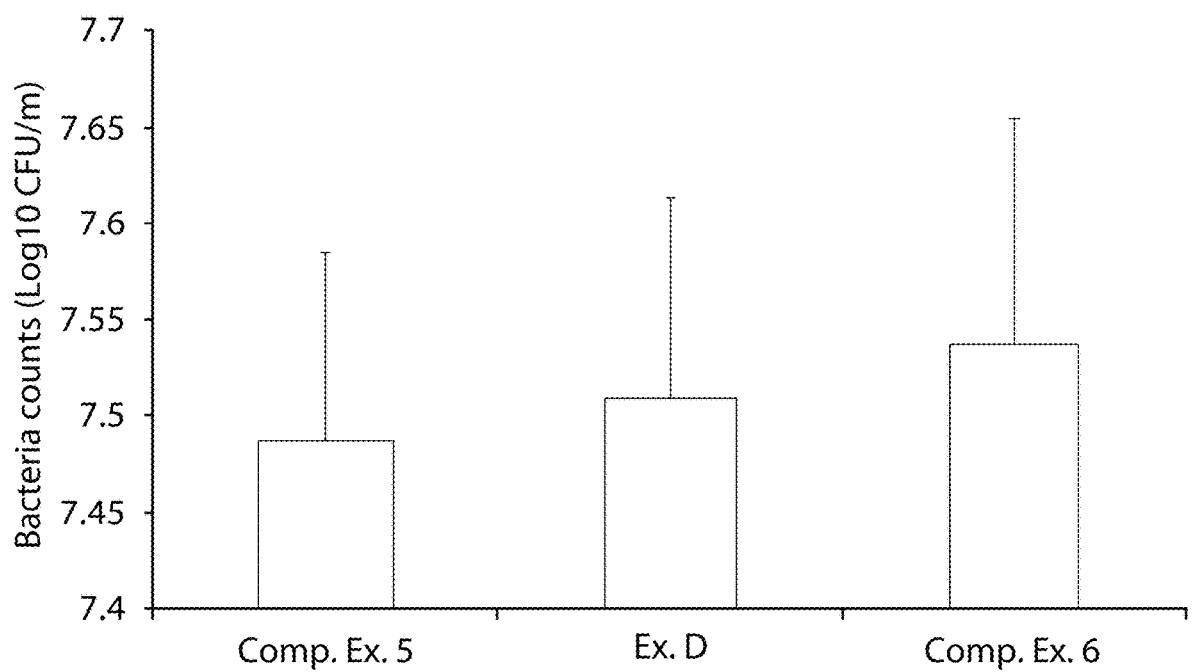
Figure 7:
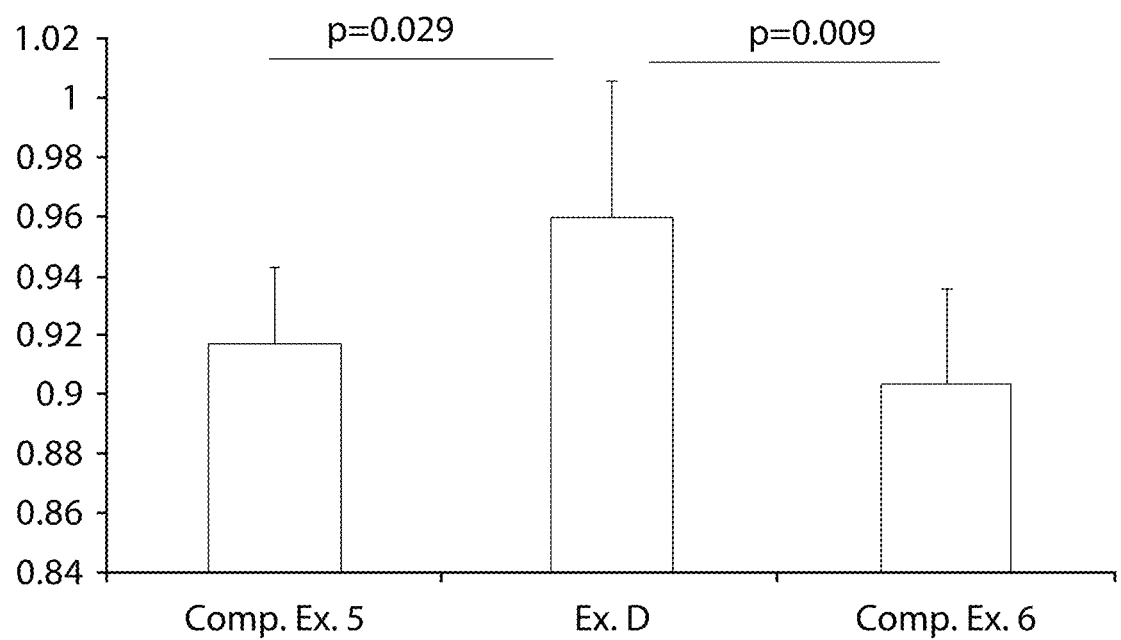
FIG. 7 is a bar graph showing the ratio of S. epidermidis to S. aureus after application of another exemplary personal care composition and comparative personal care compositions in accordance with aspects of the invention.

The turbidity of each tube was read after incubation. Replicates were run for each treatment. FIGS. 6A and 6B are bar graphs depicting the growth of *S. aureus* and *S. epidermidis* after application of Ex. D, Comp. Ex. 5, and Comp. Ex. 6. FIG. 7 is a bar graph showing the ratio of *S. epidermidis* to *S. aureus* after application of Ex. D, Comp. Ex. 5, and Comp. Ex. 6.

Example 8

Three exemplary personal care compositions (Exs. E-G) in the form of roll-on deodorants were prepared in accordance with aspects of the invention. A comparative personal composition (Comp. Ex. 7) was prepared to serve as a control. Comp. Ex. 7 was also in the form of a roll-on deodorant. The formulation for Exs. E-G and Comp. Ex. 7 are provided in Table 4, below.

TABLE 4

| US INCI Name | Ex. E (wt. %) | Ex. F (wt. %) | Ex. G (wt. %) | Comp. Ex. 7 (wt. %) |
|---|---|---|---|---|
| Water | 77.8 | 77.6 | 77.5 | 80.3 |
| Glycerin | 15 | 15 | 15 | 15 |
| Caprylyl Glycol | 0.5 | 0.5 | 0.5 | 0.5 |
| Isododecane | 1 | 1 | 1 | 1 |
| Xanthan Gum | 1 | 1 | 1 | 1 |
| Hydroxypropyl Starch Phosphate | 0.25 | 0.25 | 0.25 | 0.25 |
| Sodium Starch Octenylsuccinate | 0.75 | 0.75 | 0.75 | 0.75 |
| Triethyl Citrate | 0.5 | 0.5 | 0.5 | 0.5 |
| Fragrance | 0.3 | 0.3 | 0.3 | 0.3 |
| Sodium Benzoate | 0.4 | 0.4 | 0.4 | 0.4 |
| Ethylhexylglycerin | | 0.2 | 0.3 | |
| Lactic Acid and Sodium Lactate | 1.8 | 1.8 | 1.8 | |
| 2-Butyloctanol | 0.5 | 0.5 | 0.5 | |
| Inulin | 0.23 | 0.23 | 0.23 | |
| Fructose, Glucose, and Sucrose | 0.023 | 0.023 | 0.023 | |

Example 9

Exs. E-G were evaluated in comparison to Comp. Ex. 7 to assess the effect of the roll-on deodorant compositions on the microbiome of human skin. In particular, the growth of *S. epidermidis* and *C. striatum* in the presence of Exs. E-G and Comp. Ex. 7 was evaluated.

A TSB medium was produced using each of Exs. E-G and Comp. Ex. 7. Specifically, solutions were prepared from each of the roll-on compositions of Exs. E-G and Comp. Ex. 7 by diluting a sample from each roll-on composition to produce a respective roll-on solution containing about 20 wt. % of roll-on deodorant composition. The solutions were then added to a TSB medium.

A pure colony of *C. striatum* and *S. epidermidis* were grown in TSB medium overnight. A 2 ml sample of each bacteria culture was then separately incubated with a 2 ml sample of each respective roll-on solution at a temperature of 37° C. for 3 hours of incubation. After the incubation, the solution was 10 times series diluted in TSB medium to produce a diluted solution containing both the respective roll-on composition and the respective bacteria.

A 100 ul sample of the diluted solution was then plated on TSA plates, and incubated at a temperature of 37° C. overnight. The bacteria colonies on the TSA plates were counted the next day. At least two separate experiments were run for each tested sample, and each experiment had 3 replicates.

The data was evaluated and expressed as log 10 colony-forming unit (CFU)/ml. The ratio of desirable bacteria to undesirable bacteria was calculated by dividing the log counts of undesirable bacteria by the log counts of desirable bacteria. The statistical significance between treatments was analyzed by ANOVA at 95% confidence level in Minitab software.

Figure 8:
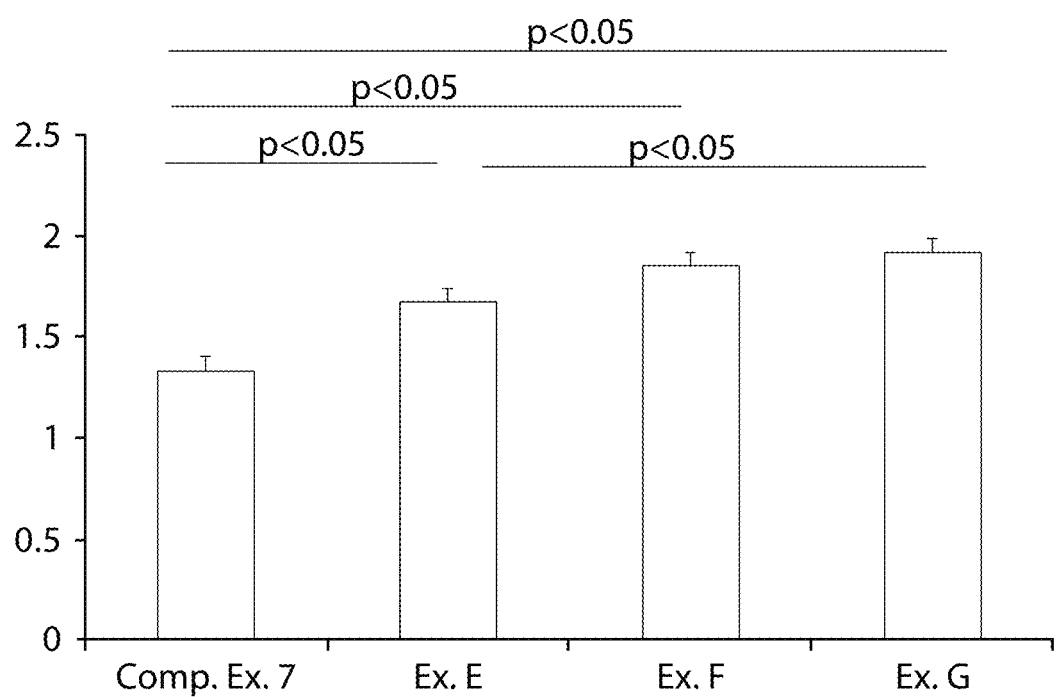
FIG. 8 is a bar graph showing the ratio of S. epidermidis to C. striatum after application of exemplary personal care compositions and comparative personal care compositions in accordance with aspects of the invention.

As seen in FIG. 8, Exs. E-G increase the ratio of desirable bacteria (*S. epidermidis*) to undesirable bacteria (*C. striatum*).

Example 10

An exemplary, non-limiting, personal care composition of the present invention (Ex. H) was prepared in accordance with aspects of the invention. A comparative personal care composition (Comp. Ex. 8) was prepared having a similar formulation as Ex. H, but did not include the polysaccharide, fatty alcohol, and post-biotic blend combination. Ex. H and Comp. Ex. 8 were in the form of a shampoo.

Example 11

Ex. H was evaluated to assess its effectiveness in reducing dandruff in comparison to Comp. Ex. 8. Specifically, Ex. H and Comp. Ex. 8 were evaluated to determine their effect on *Staphylococcus epidermidis* and *Malassezia restricta*.

A pure colony of *S. epidermidis* was grown in 10 ml of TSB medium overnight to produce a *S. epidermidis* bacteria solution. The turbidity of the bacterial culture solution was adjusted to 0.38 OD (Optical Density) using a nephelometer.

A sample from each of Ex. H and Comp. Ex. 8 was diluted with TSB medium to produce a diluted personal care solution containing 1 wt. % of the respective personal care composition. Then 2 ml of the *S. epidermidis* bacteria solution was incubated with 2 ml of the diluted personal care solution at a temperature of 35° C. for 3 hours. After completion of the 3 hours of incubation, 1 ml sample of the mixture was transferred and subsequently 7 times serially diluted in 0.85% saline up to 8 times dilution. From the 8 times dilution, 1 mL was removed and transferred to a sterile Petri plate and 15 to 20 mL of the molten Tryptic Soy agar (TSA) was added. The TSA plate was prepared using a pour plate method. The TSA plates were incubated in an inverted position at a temperature of 35° C. for 24 hours, and bacterial colonies on the respective plates were counted the next day. In total, 6 replicates were prepared for evaluating the effect of Ex. H on *S. epidermidis* and 6 replicates were prepared for evaluating the effect of Comp. Ex. 8 on *S. epidermidis*.

A pure colony of *M. restricta* was picked and was grown on Dixon's agar for 5 to 7 days at a temperature of 35° C. to produce a yeast culture solution. The turbidity of the yeast culture was adjusted to 0.8 OD (Optical Density) using a nephelometer.

A sample from each of Ex. H and Comp. Ex. 8 was diluted with TSB medium to produce a diluted personal care solution containing 1 wt. % of the respective personal care composition. Then a 2 ml of the yeast culture solution was incubated with 2 ml of the diluted personal care solution at a temperature of 35° C. for 3 hours. After completion of the 3 hour incubation, a 1 ml sample of the mixture was transferred and subsequently 10 times serially diluted in 0.85% saline up to −8 dilution. From the 8 times dilution, 1 mL was removed and transferred to a sterile Petri plate and 15 to 20 mL of the molten Dixon's agar was added. The Dixon's agar plates were incubated in an inverted position at a temperature of 35° C. for 96 hours, and colonies on the respective plates were counted. In total, 6 replicates were prepared for evaluating the effect of Ex. H on *M. restricta* and 6 replicates were prepared for evaluating the effect of Comp. Ex. 8 on *M. restricta*.

The data collected and evaluated regarding the growth of *S. epidermidis* and *M. restricta* in the presence of Ex. H or Comp. Ex. 8 was expressed as log 10 colony-forming unit (CFU)/ml. The ratio of desirable bacteria to undesirable fungi was calculated by dividing the log counts of undesirable fungi by the log counts of desirable bacteria. The statistical significance between treatments was analyzed by ANOVA at 95% confidence level in Minitab software.

Figure 9A:
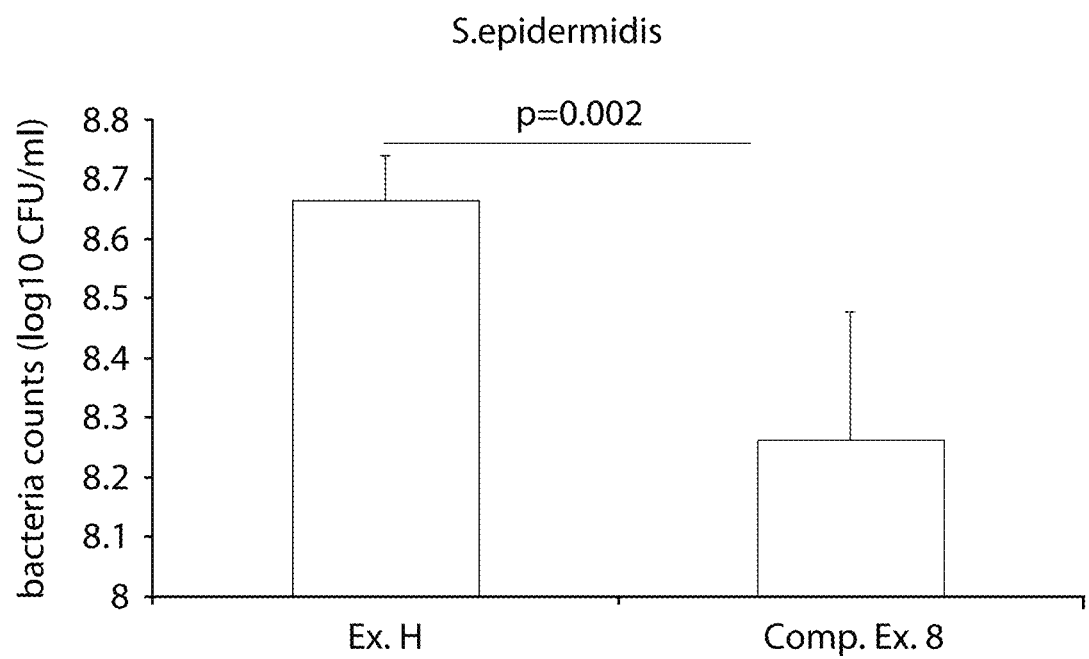
FIG. 9A is a bar graph showing the the growth of C. striatum after application of an exemplary personal care composition and comparative personal care compositions in accordance with an aspect of the invention.
Figure 9B:
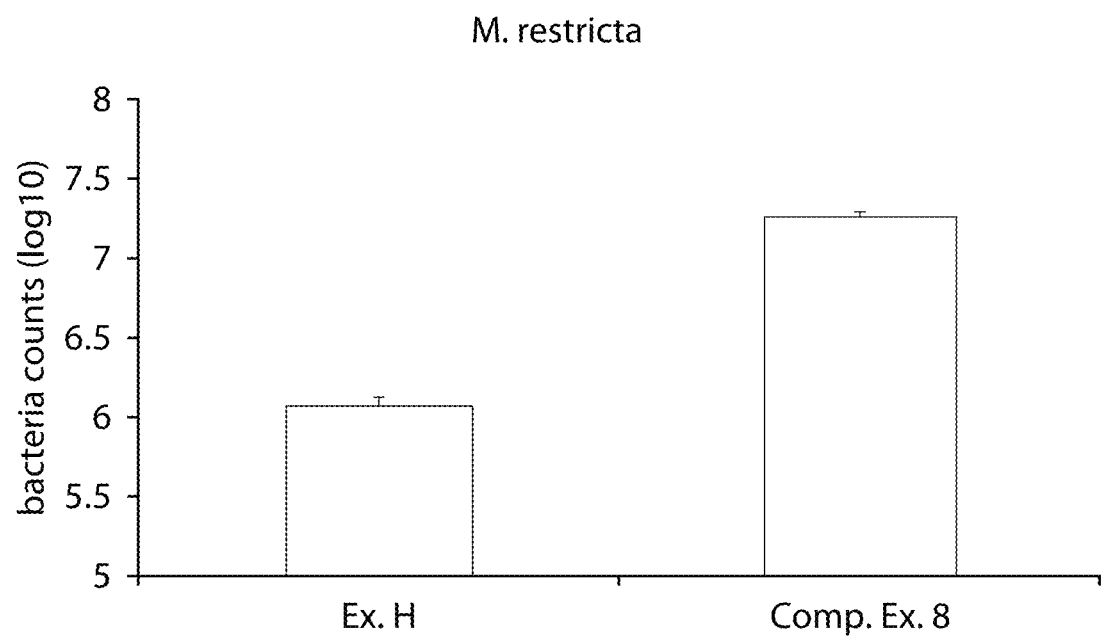
FIG. 9B is a bar graph showing the growth of M. restricta after application of an exemplary personal care composition and comparative personal care compositions in accordance with aspects of the invention.
Figure 9C:
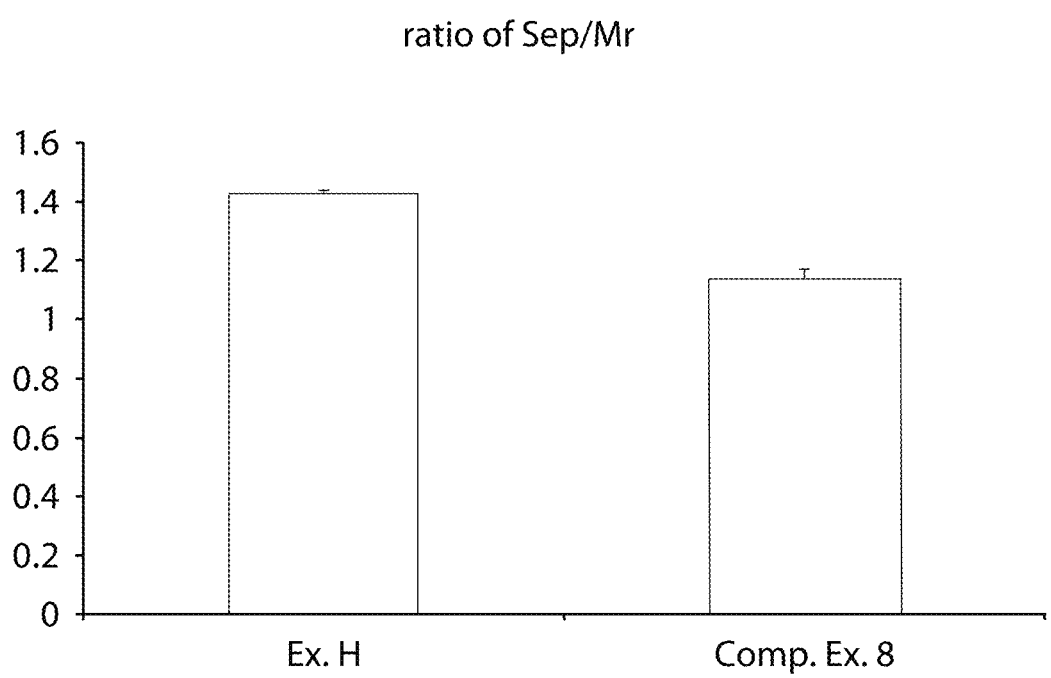
FIG. 9C is a bar graph showing the ratio of S. epidermidis to M. restricta after application of another exemplary personal care composition and comparative personal care compositions in accordance with aspects of the invention.

Bar graphs showing the results of the evaluation of Ex. H and Comp. Ex. 8 on *C. striatum* and *M. restricta* are shown in FIGS. 9A-9C.

What is claimed is:

1. A personal care composition comprising:
   a polysaccharide comprising inulin present in an amount of from about 0.1 to about 1 wt. %;
   from about 0.01 to about 12 wt. % of a fatty alcohol;
   from about 0.5 to about 7 wt. % of a post-biotic blend; and
   optionally, from about 0.1 to about 2 wt. % of ethylhexylglycerin,
   wherein all weight percentages are based on the total weight of the personal care composition;
   wherein the post-biotic blend comprises lactic acid, or a salt thereof; and pyruvic acid, or a salt thereof;
   wherein the personal care composition has a weight ratio of lactic acid, or a salt thereof, to pyruvic acid, or a salt thereof, of from about 6:1 to about 2:1;
   wherein the personal care composition is a body wash, a body lotion, a deodorant, or an antiperspirant.

2. The personal care composition according to claim 1, wherein the polysaccharide further comprises cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboxymethyl dextran, carrageenan, tragacanth gum, xanthan gum, biosaccharide gum, or a combination of two or more thereof.

3. The personal care composition according to claim 1, wherein the polysaccharide further comprises carrageenan, galacto-oligosaccharides, fructooligosaccharides, a-glucan oligosaccharide, beta glucan oligosaccharide or a combination thereof.

4. The personal care composition according to claim 1, wherein the fatty alcohol comprises butyloctanol.

5. The personal care composition according to claim 1, wherein the post-biotic blend further comprises at least one short chain fatty acid other than lactic acid and pyruvic acid or a salt thereof.

6. The personal care composition according to claim 5, wherein the at least one short chain fatty acid is selected from pentanoic acid, $CH_3CH_2CH_2CH_2COOH$, isovaleric acid, 3-methylbutanoic acid, $(CH_3)_2CHCH_2COOH$, 2-methylpropanoic acid, $(CH_3)_2CHCOOH$, butanoic acid, $CH_3CH_2CH_2COOH$, $CH_3CH_2COOH$, ethanoic acid, $CH_3COOH$, methanoic acid, HCOOH, acetic acid, butanedioic acid, succinic acid, formic acid, propionic acid, butyric acid, isobutyric acid, valeric acid, isovaleric acid, a derivative thereof, a salt thereof, and a combination of two or more thereof.

7. The personal care composition according to claim 1, wherein the post-biotic blend comprises lactic acid and a salt of pyruvic acid.

8. The personal care composition according to claim 1, wherein the personal care composition has a weight ratio of lactic acid, or a salt thereof, to pyruvic acid, or a salt thereof, of about 4:1.

9. The personal care composition according to claim 1, wherein the weight ratio of lactic acid, or a salt thereof, to pyruvic acid, or a salt thereof, is from about 5:1 to about 3:1.

10. The personal care composition according to claim 1, wherein the post-biotic blend is a biomimetic postbiotic blend adapted to mimic *lactobacillus* ferment.

11. A personal care composition comprising:
a polysaccharide comprising inulin present in an amount of from about 0.1 to about 1 wt. %;
from about 2 to about 12 wt. % of a fatty alcohol;
from about 0.5 to about 10 wt. % of a fatty ester;
from about 0.5 to about 7 wt. % of a post-biotic blend; and
optionally, from about 0.1 to about 2 wt. % of ethylhexylglycerin,
wherein all weight percentages are based on the total weight of the personal care composition;
wherein the post-biotic blend comprises lactic acid, or a salt thereof; and pyruvic acid, or a salt thereof;
wherein the personal care composition has a weight ratio of lactic acid, or a salt thereof, to pyruvic acid, or a salt thereof, of from about 6:1 to about 2:1; and
wherein the personal care composition is a body wash, a body lotion, a deodorant, or an antiperspirant.

12. The personal care composition according to claim 11, wherein the polysaccharide further comprises carrageenan.

13. The personal care composition according to claim 11, wherein the fatty alcohol comprises cetearyl alcohol, cetyl alcohol, stearyl alcohol, butyloctanol, or a combination of two or more thereof.

14. The personal care composition according to claim 11, wherein the fatty alcohol comprises butyloctanol and at least one of cetearyl alcohol, cetyl alcohol, and stearyl alcohol.

15. The personal care composition according to claim 11, wherein the fatty alcohol comprises a mixture of butyloctanol, cetearyl alcohol, cetyl alcohol, and stearyl alcohol.

16. The personal care composition according to claim 11, wherein the personal care composition is formulated to inhibit the growth of *M. restricta* by about 5% or more and increase the growth of *S. epidermidis* by about 5% or more by counting CFU/mL or reading optical density after incubating a 2 ml of a bacterial culture having an optical density of 0.8 and 0.38 at 610 nm using a UV-VIS Spectrometer for *M. restricta* and *S. epidermidis*, respectively, with a 2 ml of 1% personal care product at a temperature of 37° C. for 3 hours.

17. The personal care composition according to claim 11, wherein the composition is formulated to inhibit the growth of *M. restricta*, *C. striatum*, and *E. coli* cumulatively by about 5% or more and increase the growth of *S. epidermidis* by about 5% or more by counting CFU/mL or reading optical density after incubating a 2 ml of a bacterial culture having a 0.1 optical density at 610 nm using a UV-VIS Spectrometer for *M. restricta*, *C. striatum*, *E. coli*, and *S. epidermidis* with a 2 ml of 1% personal care product at a temperature of 37° C. for 3 hours.

\* \* \* \* \*